US008329855B2

(12) United States Patent
Usta et al.

(10) Patent No.: US 8,329,855 B2
(45) Date of Patent: Dec. 11, 2012

(54) THIENOCORONENE-IMIDE SEMICONDUCTING COMPOUNDS AND POLYMERS

(75) Inventors: Hakan Usta, Evanston, IL (US); Zhihua Chen, Skokie, IL (US); Antonio Facchetti, Chicago, IL (US)

(73) Assignees: Polyera Corporation, Skokie, IL (US); BASF SE, Ludwigshafen (DE)

( * ) Notice: Subject to any disclaimer, the term of this patent is extended or adjusted under 35 U.S.C. 154(b) by 0 days.

(21) Appl. No.: 13/095,517

(22) Filed: Apr. 27, 2011

(65) Prior Publication Data

US 2012/0264900 A1    Oct. 18, 2012

Related U.S. Application Data

(63) Continuation of application No. PCT/IB2011/051669, filed on Apr. 18, 2011.

(60) Provisional application No. 61/317,760, filed on Mar. 26, 2010.

(51) Int. Cl.
*C08G 75/00* (2006.01)

(52) U.S. Cl. .......................... 528/377; 528/370; 528/380

(58) Field of Classification Search .................. 528/377, 528/380, 370
See application file for complete search history.

(56) References Cited

OTHER PUBLICATIONS

Choi et al., Chemical Communications,(2011), 47(19), 5509-5511.*
Jiang, Wei et al., "One-pot facile synthesis of pyridyl annelated perylene bisimides," Organic Letters, 2010.vol. 12, No. 2, pp. 228-231 (2009).
Mueller, Sibylle et al., "Facile synthetic approach to novel core-extended perylene carboximide dyes," Chemical Communications, No. 32, pp. 4045-4046 (2005).
Sonia, Alibert-Fouet et al., "Liquid-crystalline and electron-deficient coronene oligocarboxylic esters and imides by twofold benzogenic Diels-Alder reactions on perylenes," Chemistry European Journal, vol. 13, No. 6, pp. 1746-1753 (2007).

* cited by examiner

*Primary Examiner* — Shane Fang
(74) *Attorney, Agent, or Firm* — Karen K. Chan

(57) ABSTRACT

Disclosed are new semiconductor materials prepared from thienocoronene-imide-based small molecule and/or polymeric compounds. Such compounds can exhibit high carrier mobility and/or good current modulation characteristics. In addition, the compounds of the present teachings can possess certain processing advantages such as solution-processability and/or good stability at ambient conditions.

17 Claims, No Drawings

THIENOCORONENE-IMIDE SEMICONDUCTING COMPOUNDS AND POLYMERS

CROSS-REFERENCE TO RELATED APPLICATIONS

This application is a continuation of International (PCT) Patent Application Serial No. PCT/IB2011/051669, filed on Apr. 18, 2011, which claims priority to and the benefit of U.S. Ser. No. 61/317,760 filed on Mar. 26, 2010, the disclosure of each of which is incorporated herein by reference.

BACKGROUND

Organic optoelectronic devices such as organic thin film transistors (OTFTS), organic light emitting diodes (OLEDs), printable circuits, organic photovoltaic devices, capacitors and sensors are fabricated using small molecule or polymeric semiconductors as their active components. To achieve high speed performance and efficient operation, it is desirable that both the p-type and n-type semiconductor materials in these organic semiconductor-based devices exhibit high charge carrier mobility ($\mu$) and stability under ambient conditions, and can be processed in a cost-effective manner.

Over the past two decades, there have been many reports on new classes of electron-depleted π-conjugated organic molecules and polymers with good semiconducting characteristics in organic field-effect transistors (OFETs). Among these, perylenediimide (PDI) derivatives have demonstrated one of the greatest potentials as n-channel semiconductors. Although there are many examples of PDI-based small molecules as high performance semiconductors for OFETs, only a few PDI polymers have been reported with charge carrier mobilities in the range of 0.001-0.02 $cm^2/V \cdot s$. Additionally, these mobility values are still one to two orders of magnitude below those obtained with small molecule PDIs and naphthalenediimide-based polymers, which probably reflect the interplay of electronic and structural features of the PDI-based polymeric backbones as a result of regioirregularity and sterically demanding monomeric unit linkage in the bay positions.

Accordingly, the art desires new small molecule and polymeric semiconductors, particularly those having good stability, processing properties, and/or charge transport characteristics in ambient conditions.

SUMMARY

In light of the foregoing, the present teachings provide thienocoronene-based molecular (small molecule) and polymeric compounds that can address various deficiencies and shortcomings of the prior art, including those outlined above. Also provided are associated devices and related methods for the preparation and use of these compounds as organic semiconductor materials. The present small molecule and polymeric compounds can exhibit properties such as good charge transport characteristics under ambient conditions, chemical stability, low-temperature processability, large solubility in common solvents, and processing versatility. As a result, field effect devices such as thin film transistors that incorporate the present compounds as the semiconductor layer can have high performance under ambient conditions, for example, demonstrating one or more of large electron mobilities, low threshold voltages, and high current on-off ratios.

In various embodiments, the present teachings provide small molecule compounds having one of the formulae below:

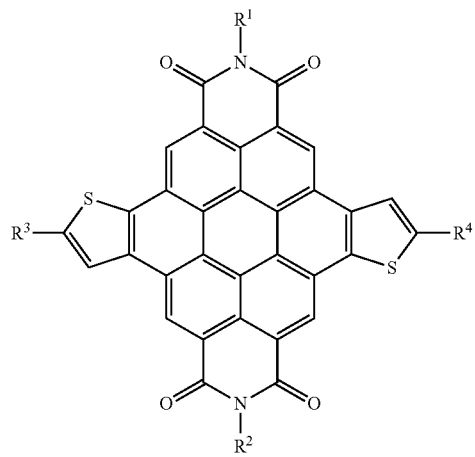

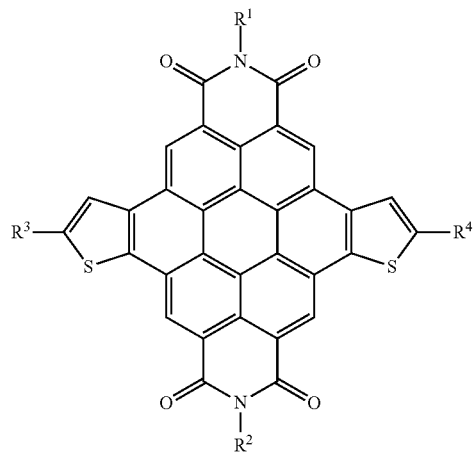

wherein $R^1$, $R^2$, $R^3$, and $R^4$ are as defined herein.

In certain embodiments, the present teachings provide polymeric compounds including repeating units having the formula:

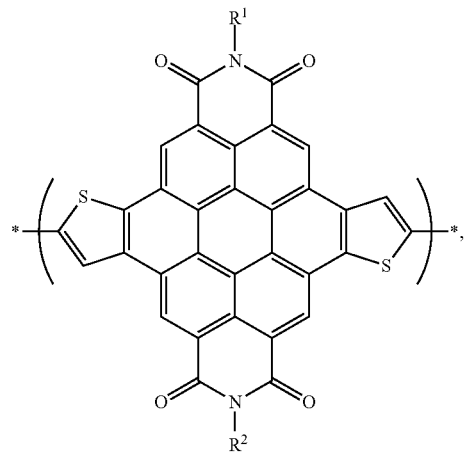

-continued

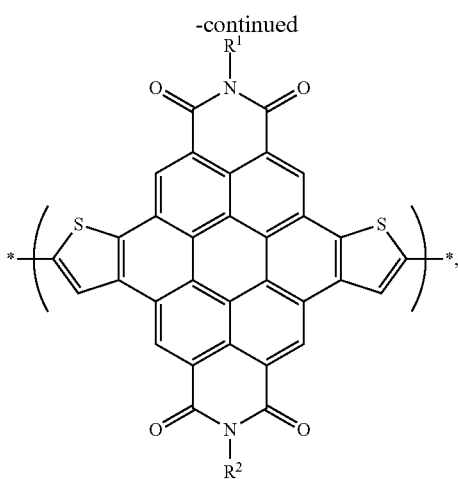

or both, wherein $R^1$ and $R^2$ are as defined herein.

For example, the present teachings can provide homopolymers consisting of repeating units having the formula:

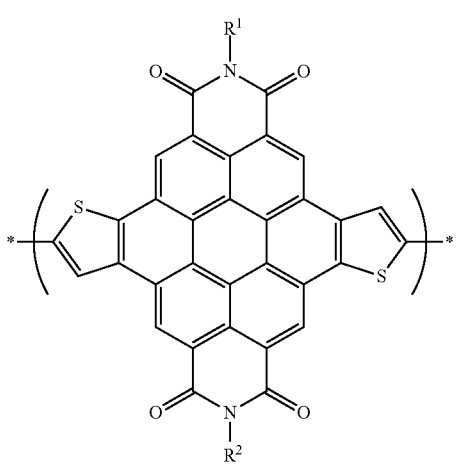

or

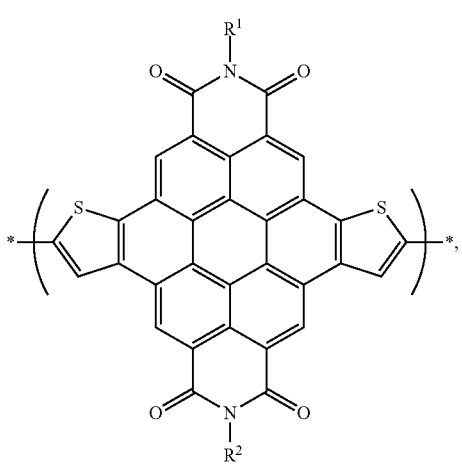

wherein $R^1$ and $R^2$ are as defined herein.

In other embodiments, the present teachings can provide copolymers including repeating units having the formula:

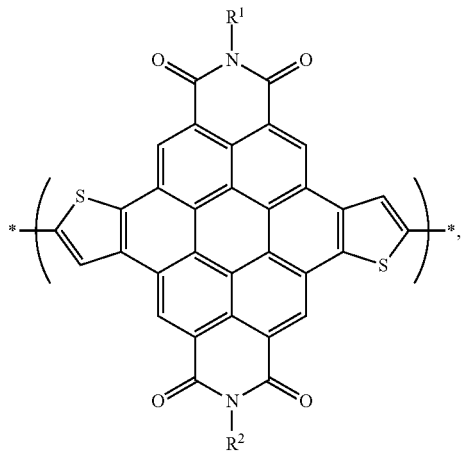

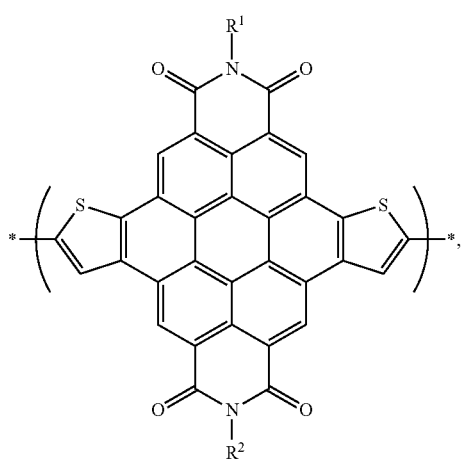

or both, and at least one other repeating unit. For example, certain copolymers according to the present teachings can include a first repeating unit $M_1$ and a second repeating unit $M_2$ and such copolymers can be represented by the formula:

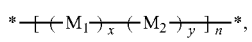

wherein:
$M_1$ has the formula:

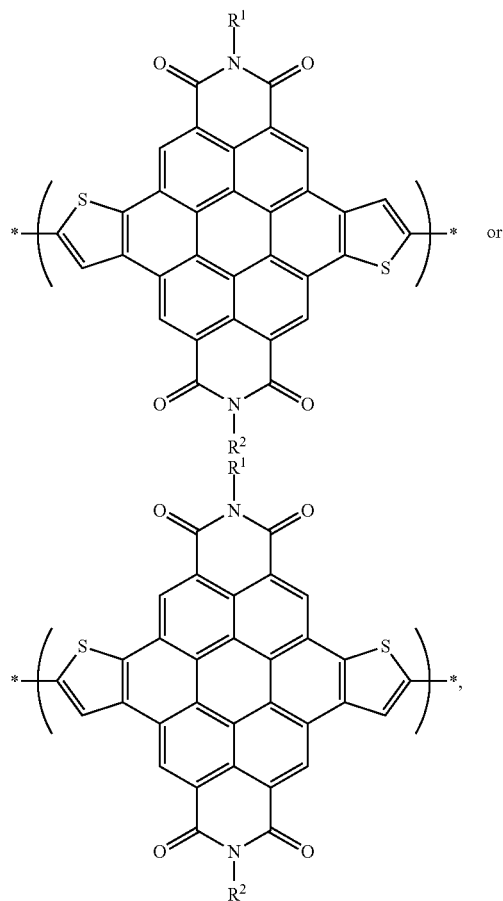

$M_2$ has a formula selected from:

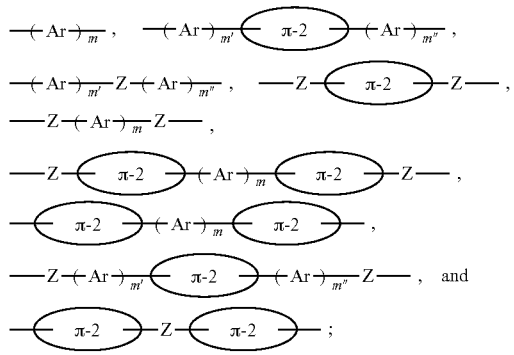

wherein:
π-2, at each occurrence, independently is an optionally substituted fused ring moiety;
Ar, at each occurrence, independently is an optionally substituted monocyclic moiety;
Z, at each occurrence, independently is a conjugated linear linker;
m, at each occurrence, is 1, 2, 3, 4, 5 or 6;
m' and m", at each occurrence, independently are 0, 1, 2, 3, 4, 5 or 6;

n is an integer in the range of 2 to 10,000; and
x and y represent the molar fraction of $M_1$ and $M_2$, respectively.

In certain embodiments, polymers of the present teachings can include those having the formula III, IV, V, VI, VII, or VIII:

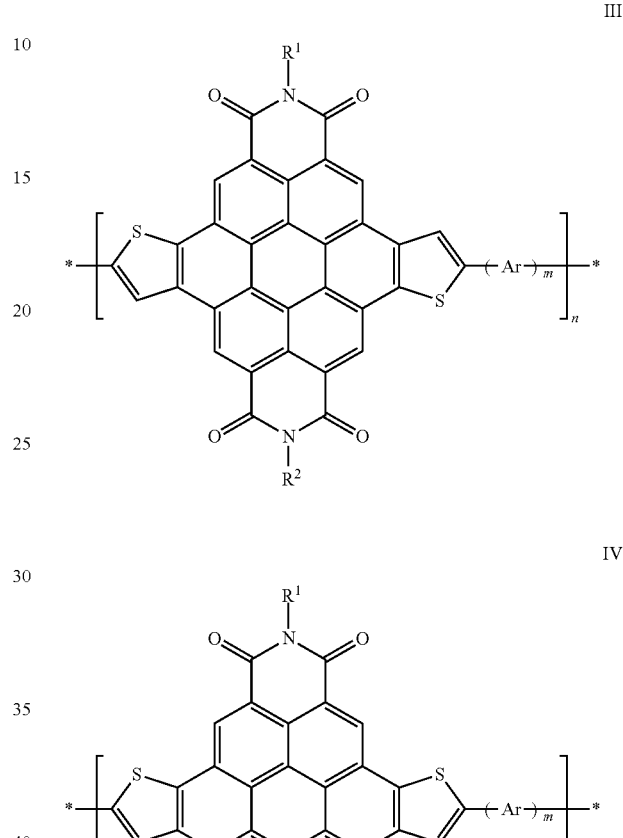

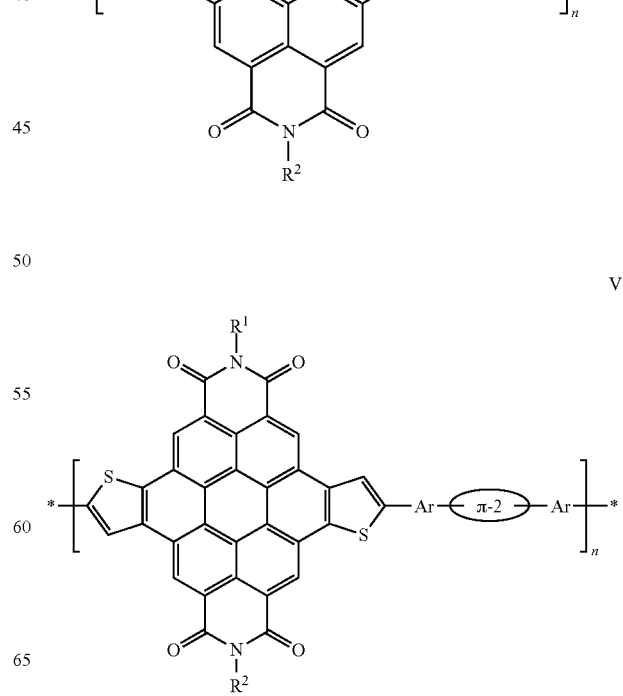

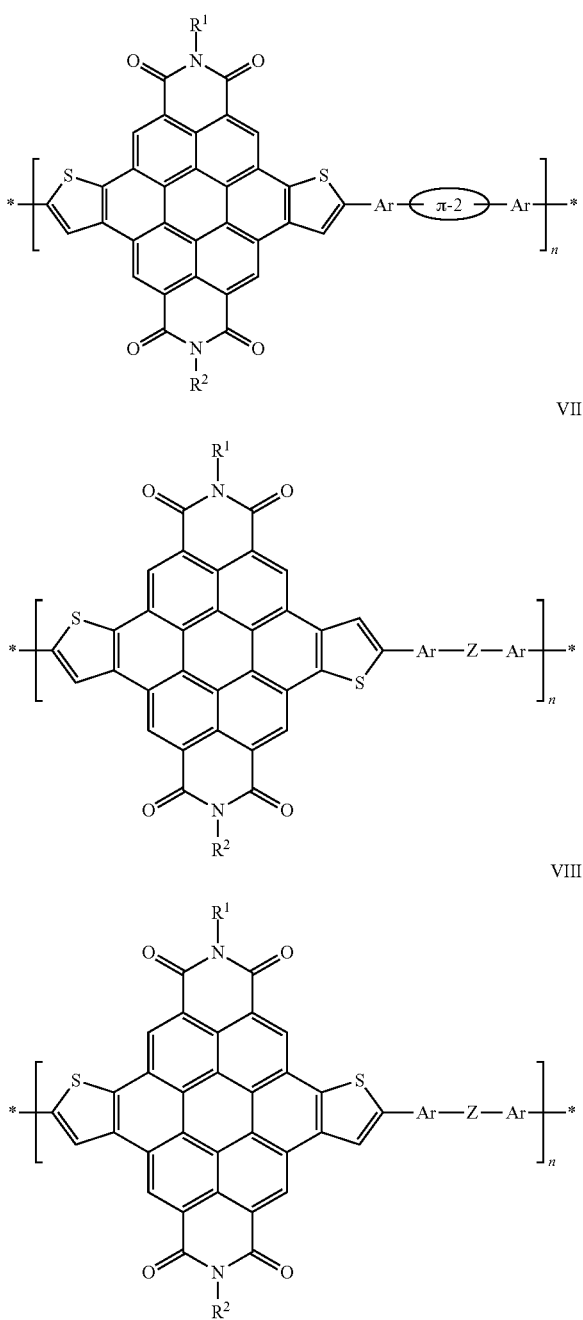

wherein R¹, R², Ar, π-2, Z, m and n are as defined herein.

The present teachings also provide methods of preparing semiconductor materials, as well as various compositions, composites, and devices that incorporate the compounds and semiconductor materials disclosed herein.

The foregoing as well as other features and advantages of the present teachings will be more fully understood from the following description, examples, and claims.

DETAILED DESCRIPTION

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_sH_{2s+1-t}X^0{}_t$, where $X^0$, at each occurrence, is F, Cl, Br or I, s is an integer in the range of 1 to 40, and t is an integer in the range of 1 to 81, provided that t is less than or equal to 2 s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O-alkyl group can be substituted as described herein.

As used herein, "alkylthio" refers to an —S-alkyl group (which, in some cases, can be expressed as —S(O)$_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which can be optionally substituted as described herein.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can include polycyclic aromatic hydrocarbons such as rylenes (or analogs thereof containing one or more heteroatoms) having the formula:

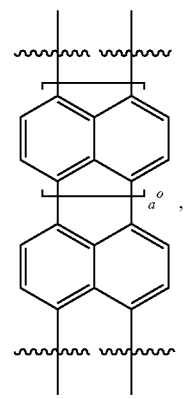

where $a^o$ can be an integer in the range of 0-3; coronenes (or analogs thereof containing one or more heteroatoms) having the formula:

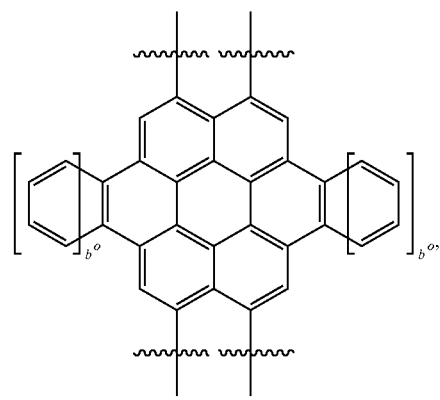

where $b^o$ can be an integer in the range of 0-3; and linear acenes (or analogs thereof containing one or more heteroatoms) having the formula:

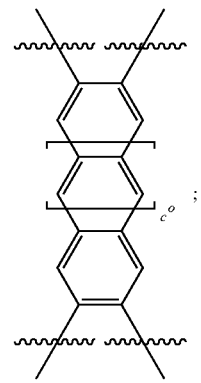

where $c^o$ can be an integer in the range of 0-4. The fused ring moiety can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., $—C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a $—Y—C_{6-14}$ aryl group, where Y is defined as a divalent alky group that can be optionally substituted as described herein. An example of an arylalkyl group is a benzyl group ($—CH_2—C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

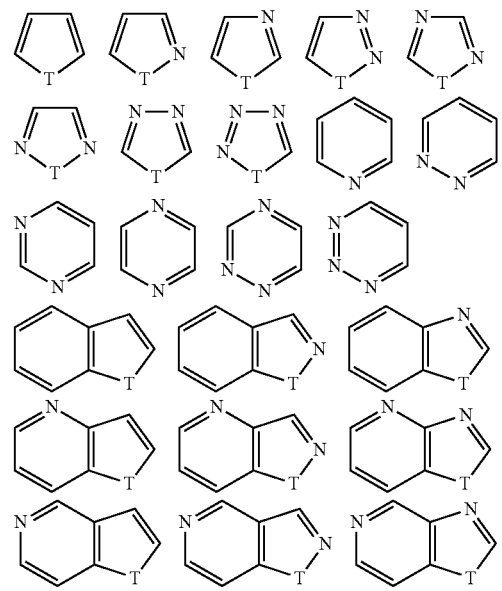

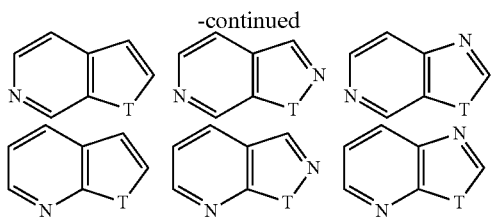

where T is O, S, NH, N-alkyl, N-aryl, N-(arylalkyl) (e.g., N-benzyl), $SiH_2$, SiH-(alkyl), $Si(alkyl)_2$, SiH-(arylalkyl), Si-$(arylalkyl)_2$, or Si(alkyl)(arylalkyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group). a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett a values. Hydrogen has a Hammett a value of zero, while other substituents have Hammett a values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group." In particular, an "electron-withdrawing group" ("EWG") or an "electron-accepting group" or an "electron-acceptor" refers to a functional group that draws electrons to itself more than a hydrogen atom would if it occupied the same position in a molecule.

Examples of electron-withdrawing groups include, but are not limited to, halogen or halo (e.g., F, Cl, Br, I), $—NO_2$, —CN, —NC, $—S(R^o)_2{}^+$, $—N(R^o)_3{}^+$, $—SO_3H$, $—SO_2R^o$, $—SO_3R^o$, $—SO_2NHR^o$, $—SO_2N(R^o)_2$, —COOH, $—COR^o$, $—COOR^o$, $—CONHR^o$, $—CON(R^o)_2$, $C_{1-40}$ haloalkyl groups, $C_{6-14}$ aryl groups, and 5-14 membered electron-poor heteroaryl groups; where $R^o$ is a $C_{1-40}$ alkyl group, a $C_{2-40}$ alkenyl group, a $C_{2-40}$ alkynyl group, a $C_{1-40}$ haloalkyl group, a $C_{1-40}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein.

It should be understood that the term "electron-donating group" can be used synonymously herein with "electron donor." In particular, an "electron-donating group" or an "electron-donor" refers to a functional group that donates electrons to a neighboring atom more than a hydrogen atom would if it occupied the same position in a molecule. Examples of electron-donating groups include —OH, $—OR^o$, $—NH_2$, $—NHR^o$, $—N(R^o)_2$, 5-14 membered electron-rich heteroaryl groups, $C_{1-40}$ alkyl groups, $C_{2-40}$ alkenyl groups, $C_{2-40}$ alkynyl groups, $C_{1-40}$ alkoxy groups, where $R^o$ is a $C_{1-40}$ alkyl group, a $C_{2-40}$ alkenyl group, a $C_{2-40}$ alkynyl group, a $C_{6-14}$ aryl group, or a $C_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one stereoisomer includes any other stereoisomer and any stereoisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconductor material" or a "p-type semiconductor" refers to a semiconductor material having holes as the majority current carriers. In some embodiments, when a p-type semiconductor material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, an "n-type semiconductor material" or an "n-type semiconductor" refers to a semiconductor material having electrons as the majority current carriers. In some embodiments, when an n-type semiconductor material is deposited on a substrate, it can provide an electron mobility in excess of about $10^{-5}$ cm$^2$/Vs. In the case of field-effect devices, an n-type semiconductor can also exhibit a current on/off ratio of greater than about 10.

As used herein, "mobility" refers to a measure of the velocity with which charge carriers, for example, holes (or units of positive charge) in the case of a p-type semiconductor material and electrons in the case of an n-type semiconductor material, move through the material under the influence of an electric field. This parameter, which depends on the device architecture, can be measured using a field-effect device or space-charge limited current measurements.

The present teachings provide various semiconducting small molecule and polymeric compounds as well as compositions and organic semiconductor materials prepared from such compounds and compositions. The organic semiconductor materials disclosed herein can exhibit useful electrical properties and can be solution-processable, e.g., spin-coatable and printable. In addition, these materials can be considered a p-type semiconductor or an n-type semiconductor depending on the functionalization of the coronene core moiety. The semiconductor materials disclosed herein can be used to fabricate various organic electronic articles, structures and devices, including field-effect transistors, unipolar circuitries, complementary circuitries, and photovoltaic devices.

More specifically, the present teachings relate to thienocoronene-based molecules, homopolymers, and copolymers, with the thienocoronene unit optionally substituted at its imide position(s) with various moieties for improved solubility while maintaining π-π interactions/intermolecular coupling for efficient charge transport. For a small molecule semiconductor, α,ω-substitution at the two thienyl rings also can tune the core's molecular structure and energy. Generally, the optional thienyl α,ω-substitution in the small molecule embodiments, the presence of any co-monomer unit(s) in the polymer embodiments, the imide position functionalization of the thienocoronene component in either the small molecule or the polymer embodiments, and any additional functionalization on either the thienocoronene component and/or the co-monomer can be affected by one or more of the following considerations: 1) the electron-withdrawing capability for air processing and operation; 2) the regiochemistry of the polymerization; 3) the core planarity and linearity of the polymer chain; 4) the capability of attachment to the π-conjugated core; 5) the potential for increased solubility of the semiconductor for solution processing; and 6) the achievement of strong π-π interactions/intermolecular coupling. The resulting small molecules and polymers can be employed as active materials in various optoelectronic devices to enhance device performance.

In one aspect, the present teachings provide small molecule compounds having formula I or II:

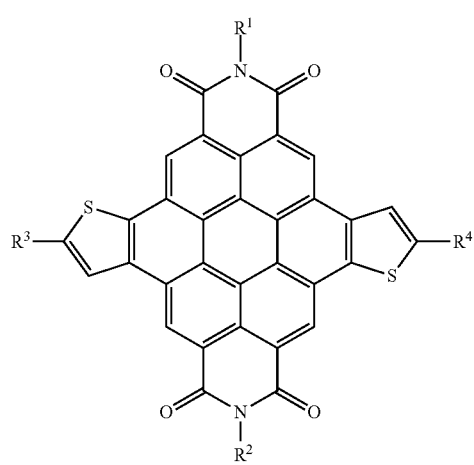

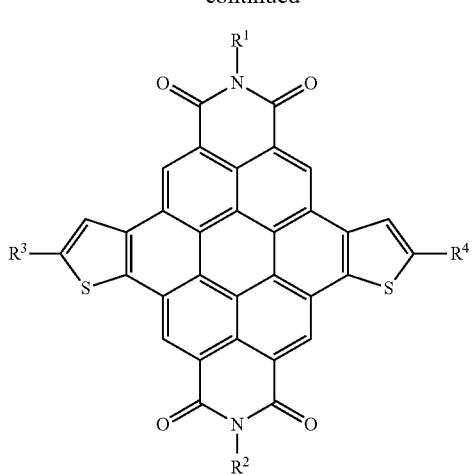

wherein $R^1$, $R^2$, $R^3$, and $R^4$ independently can be H or a substituent which can impart improved desirable properties to the compound as a whole. For example, certain substituents including one or more electron-withdrawing or electron-donating moieties can modulate the electronic properties of the compound, while substituents that include one or more aliphatic chains can improve the solubility of the compound in organic solvents.

For example, in various embodiments, $R^1$ and $R^2$ independently can be H or a substituent including one or more aliphatic chains that can improve the solubility of the compound in organic solvents.

Accordingly, in certain embodiments, $R^1$ and $R^2$ independently can be a linear or branched $C_{3-40}$ alkyl group, examples of which include an n-hexyl group, an n-octyl group, an n-dodecyl group, a 1-methylpropyl group, a 1-methylbutyl group, a 1-methylpentyl group, a 1-methylhexyl group, a 1-ethylpropyl group, a 1-ethylbutyl group, a 1,3-dimethylbutyl group, a 2-ethylhexyl group, a 2-hexyloctyl group, a 2-octyldodecyl group, and a 2-decyltetradecyl group. In certain embodiments, $R^1$ and $R^2$ independently can be a linear or branched $C_{3-40}$ alkenyl group (such as the linear or branched $C_{3-40}$ alkyl groups specified above but with one or more saturated bonds replaced by unsaturated bonds). In particular embodiments, $R^1$ and $R^2$ independently can be a branched $C_{3-20}$ alkyl group or a branched $C_{3-20}$ alkenyl group.

In certain embodiments, $R^1$ and $R^2$ independently can be a linear or branched $C_{6-40}$ alkyl or alkenyl group, an arylalkyl group (e.g., a benzyl group) substituted with a linear or branched $C_{6-40}$ alkyl or alkenyl group, an aryl group (e.g., a phenyl group) substituted with a linear or branched $C_{6-40}$ alkyl or alkenyl group, or a biaryl group (e.g., a biphenyl group) substituted with a linear or branched $C_{6-40}$ alkyl or alkenyl group, wherein each of these groups optionally can be substituted with 1-5 halo groups (e.g., F). In some embodiments, $R^1$ and $R^2$ independently can be a biaryl group wherein the two aryl groups are covalently linked via a linker. For example, the linker can be a divalent $C_{1-40}$ alkyl group wherein one or more non-adjacent $CH_2$ groups optionally can be replaced by —O—, —S—, or —Se—, i.e., O, S, and/or Se atoms are not linked directly to one another. The linker can include other heteroatoms and/or functional groups as described herein.

More generally, $R^1$ and $R^2$ independently can be selected from H, a $C_{1-40}$ alkyl group, a $C_{2-40}$ alkenyl group, a $C_{1-40}$ haloalkyl group, and 1-4 cyclic moieties, wherein:

each of the $C_{1-40}$ alkyl group, the $C_{2-40}$ alkenyl group, and the $C_{1-40}$ haloalkyl group optionally can be substituted with 1-10 substituents independently selected from a halogen, —CN, $NO_2$, OH, —$NH_2$, —NH($C_{1-40}$ alkyl), —N($C_{1-40}$ alkyl)$_2$, —S(O)$_2$OH, —CHO, —C(O)—$C_{1-40}$ alkyl, —C(O)OH, —C(O)—O$C_{1-40}$ alkyl, —C(O)$NH_2$, —C(O)NH—$C_{1-40}$ alkyl, —C(O)N($C_{1-40}$ alkyl)$_2$, —O$C_{1-40}$ alkyl, —$SiH_3$, —SiH($C_{1-40}$ alkyl)$_2$, —$SiH_2$($C_{1-40}$ alkyl), and —Si($C_{1-40}$ alkyl)$_3$;

each of the $C_{1-40}$ alkyl group, the $C_{2-40}$ alkenyl group, and the $C_{1-40}$ haloalkyl group can be bonded covalently to the imide nitrogen atom directly or via an optional linker; and each of the 1-4 cyclic moieties can be the same or different, can be bonded covalently to each other or the imide nitrogen via an optional linker, and optionally can be substituted with 1-8 substituents independently selected from a halogen, oxo, —CN, $NO_2$, OH, =C(CN)$_2$, —$NH_2$, —NH($C_{1-40}$ alkyl), —N($C_{1-40}$ alkyl)$_2$, —S(O)$_2$OH, —CHO, —C(O)OH, —C(O)—$C_{1-40}$ alkyl, —C(O)—O$C_{1-40}$ alkyl, —C(O)$NH_2$, —C(O)NH—$C_{1-40}$ alkyl, —C(O)N($C_{1-40}$ alkyl)$_2$, —$SiH_3$, —SiH($C_{1-40}$ alkyl)$_2$, —$SiH_2$($C_{1-40}$ alkyl), —Si($C_{1-40}$ alkyl)$_3$, —O—$C_{1-40}$ alkyl, —O—$C_{1-40}$ alkenyl, —O—$C_{1-40}$ haloalkyl, a $C_{1-40}$ alkyl group, a $C_{1-40}$ alkenyl group, and a $C_{1-40}$ haloalkyl group.

To further illustrate, in certain embodiments, $R^1$ and $R^2$ independently can be selected from H or -L-R, where R is selected from a $C_{1-40}$ alkyl group, a $C_{2-40}$ alkenyl group, and a $C_{1-40}$ haloalkyl group, each of which optionally can be substituted with 1-10 substituents independently selected from a halogen, —CN, $NO_2$, OH, —$NH_2$, —NH($C_{1-40}$ alkyl), —N($C_{1-40}$ alkyl)$_2$, —S(O)$_2$OH, —CHO, —C(O)—$C_{1-40}$ alkyl, —C(O)OH, —C(O)—O$C_{1-40}$ alkyl, —C(O)$NH_2$, —C(O)NH—$C_{1-40}$ alkyl, —C(O)N($C_{1-40}$ alkyl)$_2$, —O$C_{1-40}$ alkyl, —$SiH_3$, —SiH($C_{1-40}$ alkyl)$_2$, —$SiH_2$($C_{1-40}$ alkyl), and —Si($C_{1-40}$ alkyl)$_3$; and L is a covalent bond or a linker comprising one or more heteroatoms. For example, L can be a linker selected from —Y—O—Y—, —Y—[S(O)$_w$]—Y—, —Y—C(O)—Y—, —Y—[NR$^c$C(O)]—Y—, —Y—[C(O)NR$^c$]—, —Y—NR$^c$—Y—, —Y—[SiR$^c{}_2$]—Y—, where Y, at each occurrence, independently is selected from a divalent $C_{1-40}$ alkyl group, a divalent $C_{2-40}$ alkenyl group, a divalent $C_{1-40}$ haloalkyl group, and a covalent bond; $R^c$ is selected from H, a $C_{1-6}$ alkyl group, a $C_{6-14}$ aryl group, and a —$C_{1-6}$ alkyl-$C_{6-14}$ aryl group; and w is 0, 1, or 2. In some embodiments, $R^1$ and $R^2$ independently can be selected from H, a $C_{1-40}$ alkyl group, a $C_{2-40}$ alkenyl group, $C_{1-40}$ haloalkyl group, —$C_{1-40}$ alkyl-phenyl and a —Y—$C_{3-8}$-cycloalkyl, wherein Y is selected from a divalent $C_{1-40}$ alkyl group, a divalent $C_{1-40}$ haloalkyl group, and a covalent bond, and the phenyl group and the cycloalkyl group optionally can be substituted with 1-5 substituents independently selected from a halogen, a $C_{1-6}$ alkyl group, a $C_{1-6}$ alkoxy group, and a $C_{1-6}$ haloalkyl group. In particular embodiments, $R^1$ and $R^2$ independently can be selected from H, a $C_{3-40}$ alkyl group, a $C_{4-40}$ alkenyl group, and a $C_{3-40}$ haloalkyl group, and an —O—$C_{3-40}$ alkyl group, where each of these groups can be linear or branched, and can be optionally substituted as described herein.

In other embodiments, $R^1$ and $R^2$ independently can include one or more cyclic moieties. For example, $R^1$ and $R^2$ independently can be selected from -L-Cy$^1$, -L'-Cy$^1$-L'-Cy$^2$, -L'-Cy$^1$-L'-Cy$^2$—Cy$^2$, -L-Cy$^1$—Cy$^1$, -L-Cy$^1$—Cy$^1$-L-Cy$^2$, -L'-Cy$^1$—Cy$^1$-L'-Cy$^2$—Cy$^2$, -L'-Cy$^1$-L-R, -L'-Cy$^1$-L'-Cy$^2$-L-R, -L'-Cy$^1$-L'-Cy$^2$—Cy$^2$-L-R, -L'-Cy$^1$—Cy$^1$-L-R, and -L-Cy$^1$—Cy$^1$-L-Cy$^2$-L-R; wherein:

Cy$^1$ and Cy$^2$ independently can be selected from a C$_{6-14}$ aryl group, a 5-14 membered heteroaryl group, a C$_{3-14}$ cycloalkyl group, and a 3-14 membered cycloheteroalkyl group, each of which optionally can be substituted with 1-5 substituents independently selected from a halogen, —CN, oxo, =C(CN)$_2$, a C$_{1-6}$ alkyl group, a C$_{1-6}$ alkoxy group, and a C$_{1-6}$ haloalkyl group;

L', at each occurrence, independently can be a covalent bond or a linker selected from —Y—O—Y—, —Y—[S(O)$_w$]—Y—, —Y—C(O)—Y—, —Y—[NR$^c$C(O)]—Y—, —Y—[C(O)NR$^c$]—, —Y—NR$^c$—Y—, —Y—[SiR$^c_2$]—Y—, a divalent C$_{1-40}$ alkyl group, a divalent C$_{2-40}$ alkenyl group, and a divalent C$_{1-40}$ haloalkyl group, where Y, R, R$^c$, and w are as defined above.

Further examples of R$^1$ and R$^2$ include:

1) linear or branched C$_{1-40}$ alkyl groups and C$_{2-40}$ alkenyl groups such as:

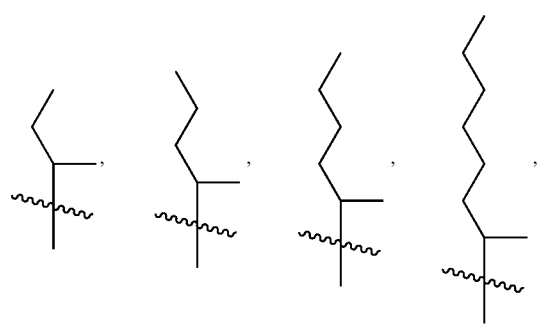

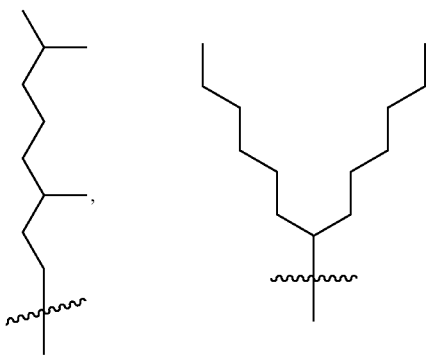

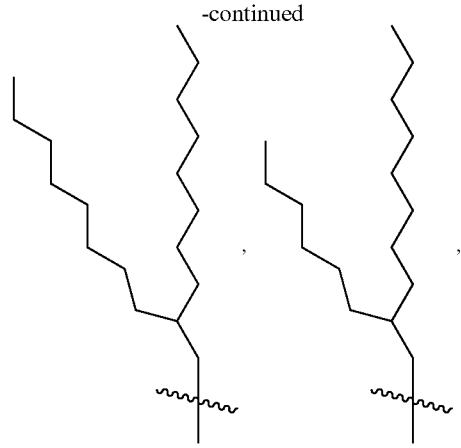

-continued

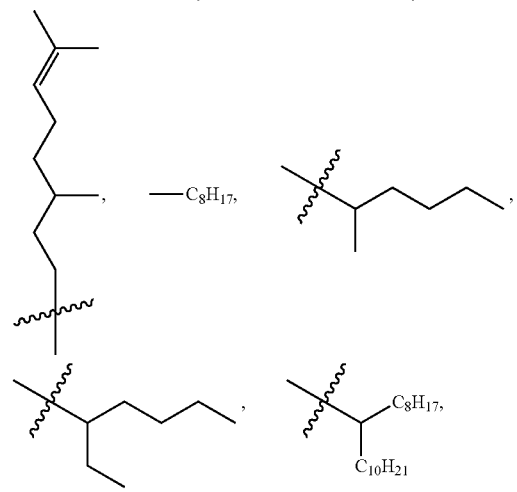

2) optionally substituted cycloalkyl groups such as:

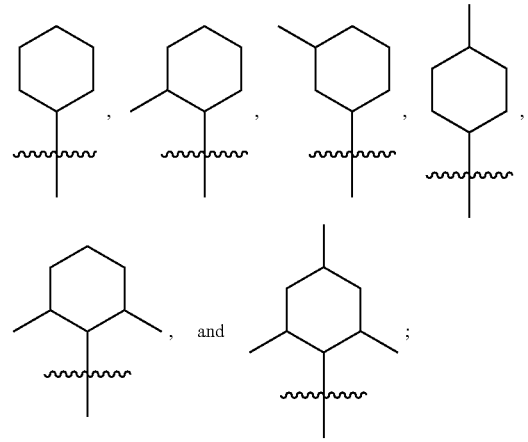

and
3) optionally substituted aryl groups, arylalkyl groups, biaryl groups, biarylalkyl groups such as:

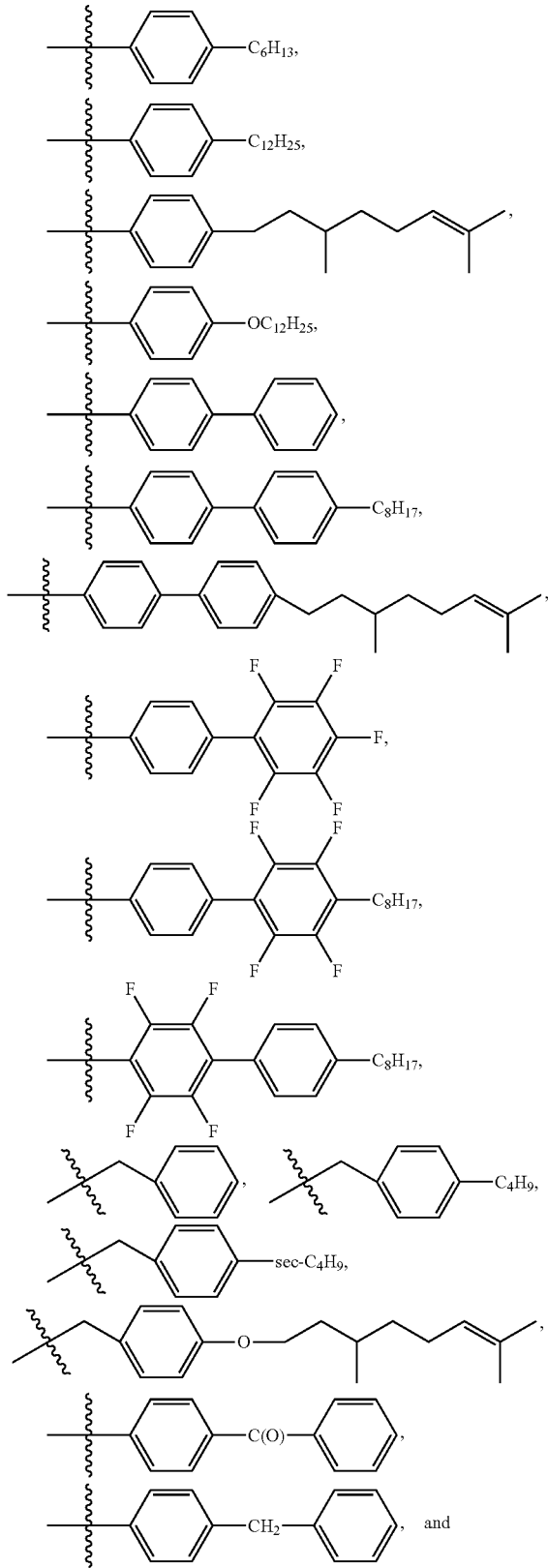

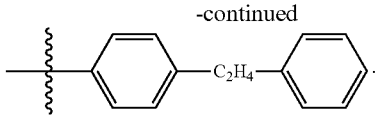

In various embodiments, $R^3$ and $R^4$ independently can be H or $R^a$, wherein:

$R^a$, at each occurrence, is a) halogen, b) —CN, c) —NO$_2$, d) —OR$^f$, e) —SR$^f$, f) —NR$^g$R$^h$, g) —N(O)R$^g$R$^h$, h) —S(O)$_q$R$^g$, i) —S(O)$_q$OR$^g$, j) —S(O)$_q$NR$^g$R$^h$, k) —C(O)R$^g$, l) —C(O)OR$^f$, m) —C(O)NR$^g$R$^h$, n) —C(S)NR$^g$R$^h$, o) —SiH$_3$, p) —SiH(C$_{1-20}$ alkyl)$_2$, q) —SiH$_2$(C$_{1-20}$ alkyl), r) —Si(C$_{1-20}$ alkyl)$_3$, s) a C$_{1-20}$ alkyl group, t) a C$_{2-20}$ alkenyl group, u) a C$_{2-20}$ alkynyl group, v) a C$_{1-20}$ haloalkyl group, w) a —Y—C$_{3-14}$ cycloalkyl group, x) a —Y—C$_{6-14}$ aryl group, y) a —Y-3-14 membered cycloheteroalkyl group, or z) a —Y-5-14 membered heteroaryl group, wherein each of the C$_{1-20}$ alkyl group, the C$_{2-20}$ alkenyl group, the C$_{2-20}$ alkynyl group, the C$_{3-14}$ cycloalkyl group, the C$_{6-14}$ aryl group, the 3-14 membered cycloheteroalkyl group, and the 5-14 membered heteroaryl group optionally is substituted with 1-4 $R^i$ groups;

$R^f$, at each occurrence, is a) H, b) —C(O)R$^g$, c) —C(O)NR$^g$R$^h$, d) —C(S)R$^g$, e) —C(S)NR$^g$R$^h$, f) a C$_{1-20}$ alkyl group, g) a C$_{2-20}$ alkenyl group, h) a C$_{2-20}$ alkynyl group, i) a C$_{3-14}$ cycloalkyl group, j) a C$_{6-14}$ aryl group, k) a 3-14 membered cycloheteroalkyl group, or l) a 5-14 membered heteroaryl group, wherein each of the C$_{1-20}$ alkyl group, the C$_{2-20}$ alkenyl group, the C$_{2-20}$ alkynyl group, the C$_{3-14}$ cycloalkyl group, the C$_{6-14}$ aryl group, the 3-14 membered cycloheteroalkyl group, and the 5-14 membered heteroaryl group optionally is substituted with 1-4 $R^i$ groups;

$R^g$ and $R^h$, at each occurrence, independently are a) H, b) —OH, c) —SH, d) —S(O)$_2$OH, e) —C(O)OH, f) —C(O)NH$_2$, g) —C(S)NH$_2$, h) —OC$_{1-10}$ alkyl, i) —C(O)—C$_{1-20}$ alkyl, j) —C(O)—OC$_{1-20}$ alkyl, k) —C(S)N(C$_{1-20}$ alkyl)$_2$, l) —C(S)NH—C$_{1-20}$ alkyl, m) —C(O)NH—C$_{1-20}$ alkyl, n) —C(O)N(C$_{1-20}$ alkyl)$_2$, o) —S(O)$_q$—C$_{1-20}$ alkyl, p) —S(O)$_q$—OC$_{1-20}$ alkyl, q) a C$_{1-20}$ alkyl group, r) a C$_{2-20}$ alkenyl group, s) a C$_{2-20}$ alkynyl group, t) a C$_{1-20}$ alkoxy group, u) a C$_{3-14}$ cycloalkyl group, v) a C$_{6-14}$ aryl group, w) a 3-14 membered cycloheteroalkyl group, or x) a 5-14 membered heteroaryl group, wherein each of the C$_{1-20}$ alkyl groups, the C$_{2-20}$ alkenyl group, the C$_{2-20}$ alkynyl group, the C$_{3-14}$ cycloalkyl group, the C$_{6-14}$ aryl group, the 3-14 membered cycloheteroalkyl group, and the 5-14 membered heteroaryl group optionally is substituted with 1-4 $R^i$ groups;

$R^i$, at each occurrence, is a) a halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —N(C$_{1-20}$ alkyl)-C$_{6-14}$ aryl, j) —N(C$_{6-14}$ aryl)$_2$, k) —S(O)$_q$H, l) —S(O)$_q$—C$_{1-20}$ alkyl, m) —S(O)$_2$OH, n) —S(O)$_q$—OC$_{1-20}$ alkyl, o) —S(O)$_q$—OC$_{6-14}$ aryl, p) —CHO, q) —C(O)—C$_{1-20}$ alkyl, r) —C(O)—C$_{6-14}$ aryl, s) —C(O)OH, t) —C(O)—OC$_{1-20}$ alkyl, u) —C(O)—OC$_{6-14}$ aryl, v) —C(O)NH$_2$, w) —C(O)NH—C$_{1-20}$ alkyl, x) —C(O)N(C$_{1-20}$ alkyl)$_2$, y) —C(O)NH—C$_{6-14}$ aryl, z) —C(O)N(C$_{1-20}$ alkyl)-C$_{6-14}$ aryl, aa) —C(O)N(C$_{6-14}$ aryl)$_2$, ab) —C(S)NH$_2$, ac) —C(S)NH—C$_{1-20}$ alkyl, ad) —C(S)N(C$_{1-20}$ alkyl)$_2$, ae) —C(S)N(C$_{6-14}$ aryl)$_2$, af) —C(S)N(C$_{1-20}$ alkyl)-C$_{6-14}$ aryl, ag) —C(S)NH—C$_{6-14}$ aryl, ah) —S(O)$_q$NH$_2$, ai)

—S(O)$_q$NH(C$_{1-20}$ alkyl), aj) —S(O)$_q$N(C$_{1-20}$ alkyl)$_2$, ak) —S(O)—NH(C$_{6-14}$ aryl), al) —S(O)$_q$N(C$_{1-20}$ alkyl)-C$_{6-14}$ aryl, am) —S(O)$_q$N(C$_{6-14}$ aryl)$_2$, an) —SiH$_3$, ao) —SiH(C$_{1-20}$ alkyl)$_2$, ap) —SiH$_2$(C$_{1-20}$ alkyl), ar) —Si(C$_{1-20}$ alkyl)$_3$, as) a C$_{1-20}$ alkyl group, at) a C$_{2-20}$ alkenyl group, au) a C$_{2-20}$ alkynyl group, av) a C$_{1-20}$ alkoxy group, aw) a C$_{1-20}$ alkylthio group, ax) a C$_{1-20}$ haloalkyl group, ay) a C$_{3-14}$ cycloalkyl group, az) a C$_{6-14}$ aryl group, ba) a 3-14 membered cycloheteroalkyl group, or bb) a 5-14 membered heteroaryl group;

Y, at each occurrence, is a divalent C$_{1-20}$ alkyl group, a divalent C$_{1-20}$ haloalkyl group, or a covalent bond; and q is 1 or 2.

For example, R$^3$ and R$^4$ independently can be selected from H, F, Cl, Br, and CN. In particular embodiments, R$^3$ and R$^4$ can be H. In other embodiments, R$^3$ and R$^4$ can be Br.

Compounds of the present teachings can include, but are not limited to, the following compounds:

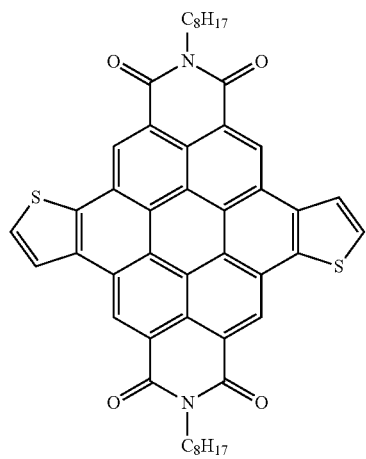

Ia

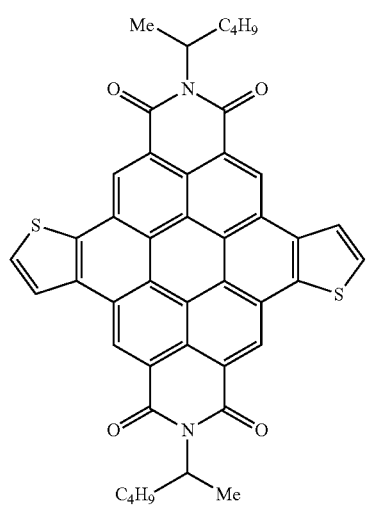

Ib

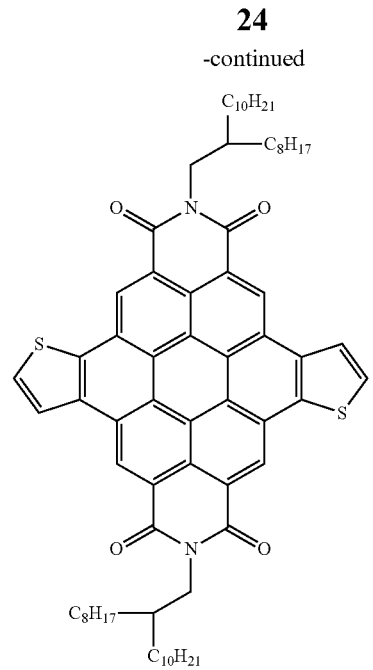

Ic

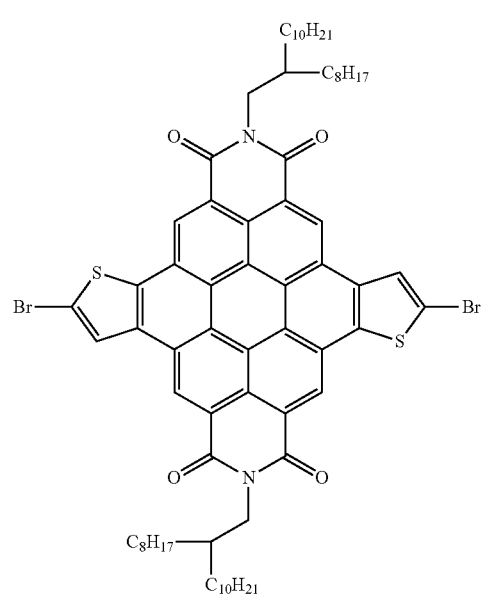

Id

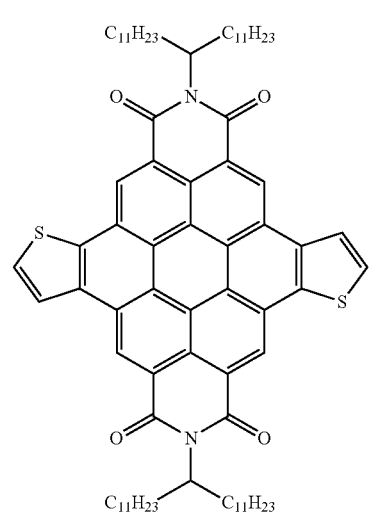

Ie

25

-continued

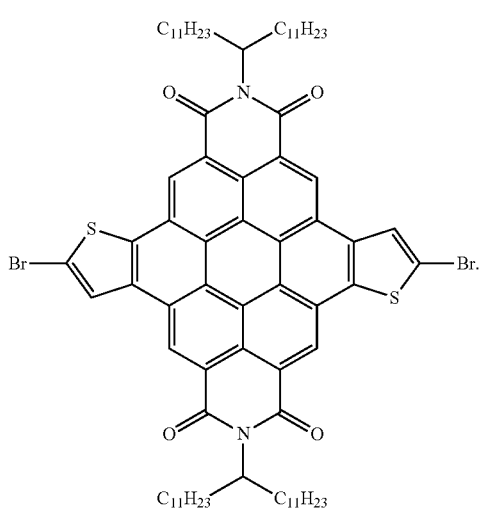

In other embodiments, the present teachings provide thienocoronene-based polymers having semiconducting activity. The present polymers can be homopolymers of repeating units:

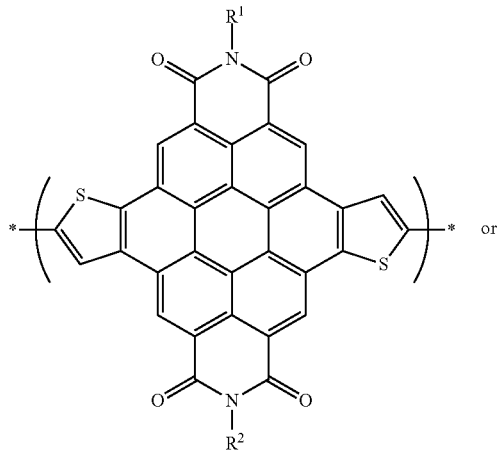

or

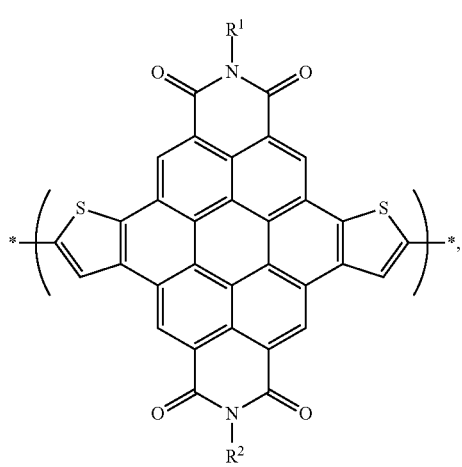

or copolymers including repeating units:

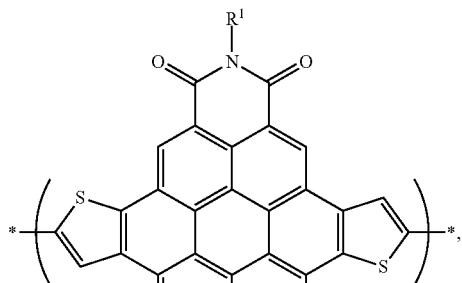

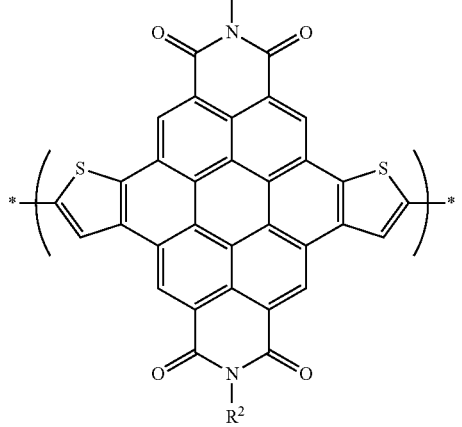

or both,
and optionally additional repeating units, where $R^1$ and $R^2$ are as defined herein. The polymers of the present teachings can exhibit semiconductor behavior such as carrier mobility and/or current modulation characteristics in a field-effect device, and light absorption/charge separation in a photovoltaic device. Further, the polymers can be associated with or embedded with other components for utilization in other semiconductor-based devices. In addition, the present polymers can possess certain processing advantages such as solution-processability, for example, printability, and/or good stability under ambient conditions, for example, air stability.

As used herein, a "polymer" or "polymeric compound" refers to a molecule (e.g., a macromolecule) including a plurality of repeating units connected by covalent chemical bonds. As used herein, a repeating unit in a polymer must repeat itself at least twice in the polymer. A polymer can be represented by the general formula:

$$*\text{-(M)-}*$$

wherein M is the repeating unit or monomer. The degree of polymerization (n) can range from 2 to greater than 10,000. The polymer can have only one type of repeating unit as well as two or more types of different repeating units. In the former case, the polymer can be referred to as a homopolymer. In the latter case, the term "copolymer" or "copolymeric compound" can be used instead, especially when the polymer includes chemically significantly different repeating units. The polymer or polymeric compound can be linear or branched. Branched polymers can include dendritic polymers, such as dendronized polymers, hyperbranched polymers, brush polymers (also called bottle-brushes), and the like. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. For example, the general formula:

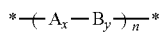

can be used to represent a copolymer of A and B having x mole fraction of A and y mole fraction of B in the copolymer, where the manner in which comonomers A and B is repeated can be alternating, random, regiorandom, regioregular, or in blocks. The degree of polymerization (n) can range from 2 to greater than 10,000.

For example, in embodiments where the polymers are homopolymers, the polymers can consist of repeating units

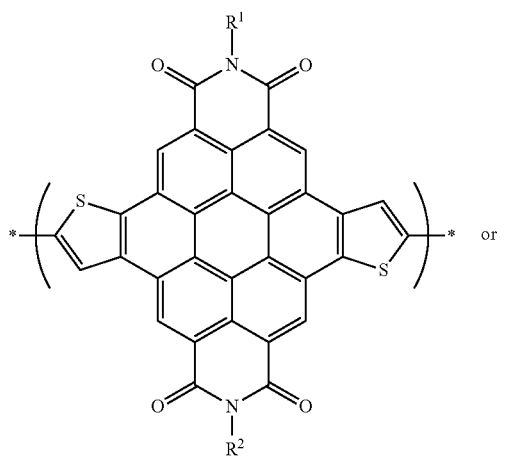

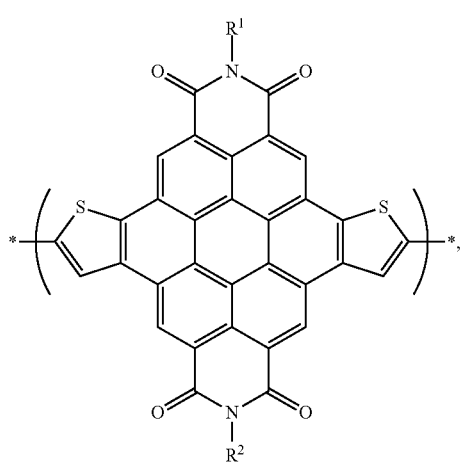

where $R^1$ and $R^2$ are as defined herein.

Accordingly, particular embodiments of the present homopolymers can have the formula:

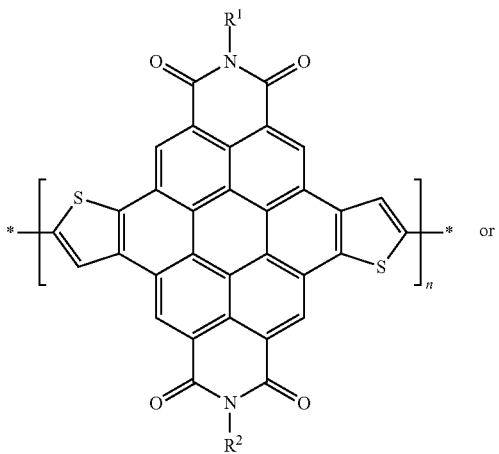

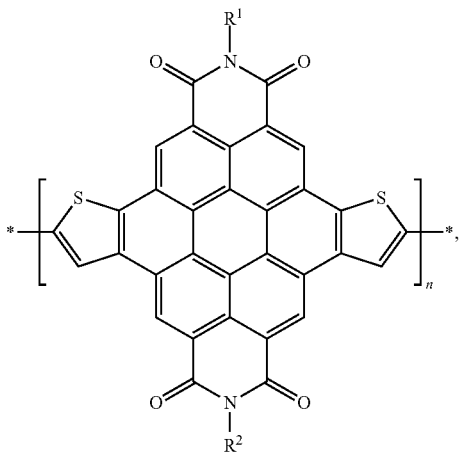

where $R^1$ and $R^2$, independently can be a linear or branched $C_{1-40}$ alkyl or haloalkyl group, and n is greater than 2. For example, n can be an integer in the range of 2 to 5,000, 2 to 1,000, 2 to 500, 2 to 400, 2 to 300, or 2 to 200. In certain embodiments, n can be 2-100. In some embodiments, n can be an integer between 3 and 1,000. In certain embodiments, n can be 4-1,000, 5-1,000, 6-1,000, 7-1,000, 8-1,000, 9-1,000, or 10-1,000. For example, n can be 8-500, 8-400, 8-300, or 8-200. In certain embodiments, n can be 8-100.

For example, an embodiment of the present homopolymers can have the formula:

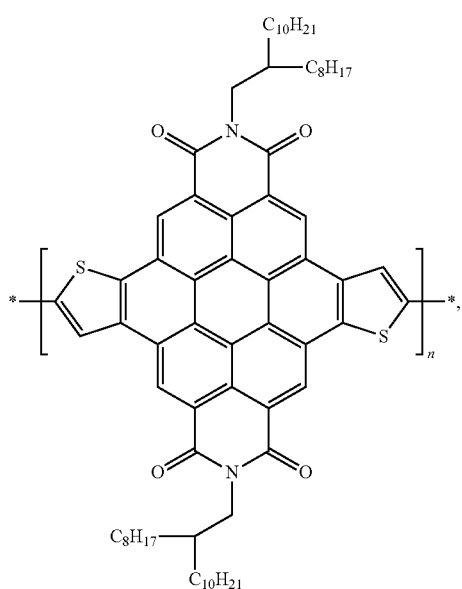

where n is an integer in the range of 2-1000, 3-1000, 4-1000, or 5-1000.

In embodiments where the polymers are copolymers, the polymers can include repeating units having the formula:

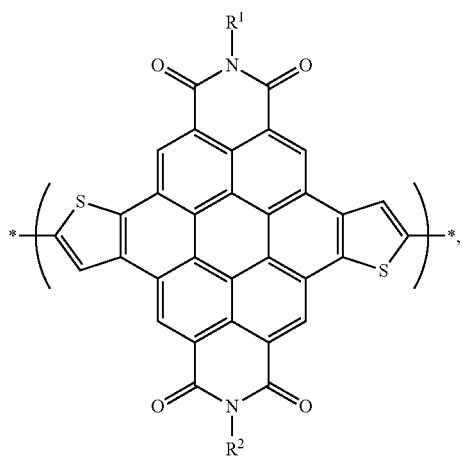

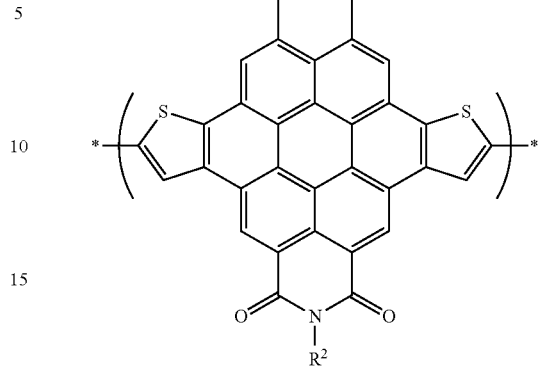

or both,
and optionally one or more other repeating units, where $R^1$ and $R^2$ are as defined herein. In certain embodiments, the polymers can be random $A_xB_y$ copolymers, where x and y represent the molar fraction of monomer A and monomer B, respectively. In other embodiments, the polymers can be alternating A-B copolymers. For example, monomer A can include an optionally substituted thienocoronene imide moiety and monomer B can include one or more optionally substituted aromatic moieties. In embodiments where monomer B includes two or more optionally substituted aromatic moieties, the two or more moieties can be linked to each other or the thienocoronene moiety via a linker as described herein. Each of monomer A and monomer B can be optionally substituted or functionalized with one or more electron-donating or electron-accepting groups.

In various embodiments, copolymers of the present teachings can include a first repeating unit $M_1$ and a second repeating unit $M_2$ and such copolymers can be represented by the formula:

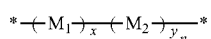

wherein:
$M_1$ has the formula:

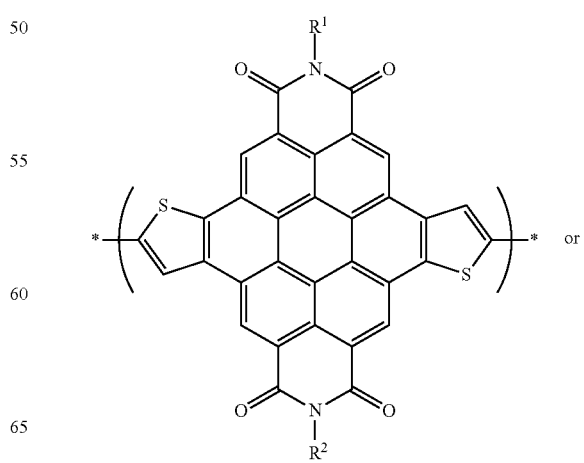

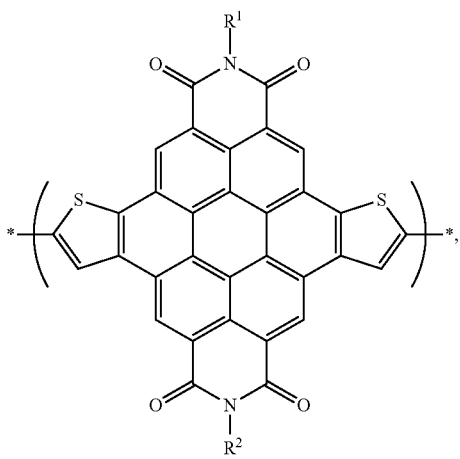

$M_2$ has a formula selected from:

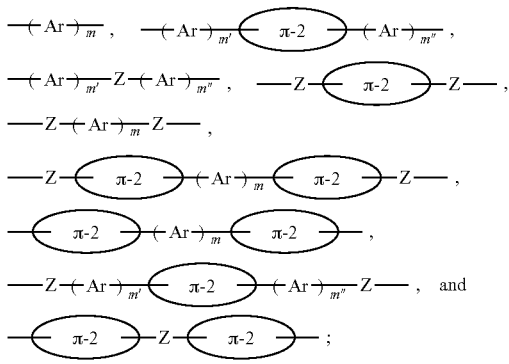

wherein:

π-2, at each occurrence, independently is an optionally substituted fused ring moiety;

Ar, at each occurrence, independently is an optionally substituted monocyclic moiety;

Z, at each occurrence, independently is a conjugated linear linker;

m, at each occurrence, is 1, 2, 3, 4, 5 or 6;

m' and m", at each occurrence, independently are 0, 1, 2, 3, 4, 5 or 6;

n is an integer in the range of 2 to 10,000; and x and y represent the molar fraction of $M_1$ and $M_2$, respectively.

In certain embodiments, the present copolymers represented by the formula:

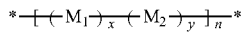

can be a random copolymer, where $M_1$, $M_2$, n, x, and y are as defined herein. In certain embodiments, copolymers represented by the above formula can include alternating copolymers, in which case, the alternating copolymers can be represented by the formula:

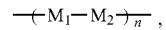

wherein $M_1$ and $M_2$ are as defined herein, and n is an integer in the range of 2 to 10,000.

For example, in the comonomer $M_1$, $R^1$ and $R^2$ independently can be a linear or branched $C_{3-40}$ alkyl group, examples of which include an n-hexyl group, an n-octyl group, an n-dodecyl group, a 1-methylpropyl group, a 1-methylbutyl group, a 1-methylpentyl group, a 1-methylhexyl group, a 1-ethylpropyl group, a 1-ethylbutyl group, a 1,3-dimethylbutyl group, a 2-ethylhexyl group, a 2-hexyloctyl group, a 2-octyldodecyl group, and a 2-decyltetradecyl group. In certain embodiments, $R^1$ and $R^2$ independently can be a linear or branched $C_{3-40}$ alkenyl group (such as the linear or branched $C_{3-40}$ alkyl groups specified above but with one or more saturated bonds replaced by unsaturated bonds). In particular embodiments, $R^1$ and $R^2$ independently can be a branched $C_{3-20}$ alkyl group or a branched $C_{3-20}$ alkenyl group.

In various embodiments, the comonomer $M_2$ can include one or more Ar moieties. Depending on whether it is located within the polymeric backbone or it constitutes one of the end groups of the polymer, Ar can be divalent or monovalent. In certain embodiments, each Ar can be independently a 5- or 6-membered aryl or heteroaryl group. For example, each Ar can be selected from a phenyl group, a thienyl group, a furyl group, a pyrrolyl group, an isothiazolyl group, a thiazolyl group, a 1,2,4-thiadiazolyl group, a 1,3,4-thiadiazolyl group, and a 1,2,5-thiadiazolyl group, wherein each group can be divalent or monovalent, and optionally can be substituted with 1-4 substituents independently selected from a halogen, —CN, an oxo group, a $C_{1-6}$ alkyl group, a $C_{1-6}$ alkoxy group, a $C_{1-6}$ haloalkyl group, $NH_2$, $NH(C_{1-6}$ alkyl) and $N(C_{1-6}$ alkyl)$_2$. In particular embodiments, each Ar can be selected from a thienyl group, an isothiazolyl group, a thiazolyl group, a 1,2,4-thiadiazolyl group, a 1,3,4-thiadiazolyl group, a 1,2,5-thiadiazolyl group, a phenyl group, and a pyrrolyl group, wherein each group optionally can be substituted with 1-2 substituents independently selected from a halogen, —CN, an oxo group, a $C_{1-6}$ alkyl group, a $C_{1-6}$ alkoxy group, a $C_{1-6}$ haloalkyl group, $NH_2$, $NH(C_{1-6}$ alkyl) and $N(C_{1-6}$ alkyl)$_2$. In some embodiments, Ar can be unsubstituted. In some embodiments, Ar can be a thienyl group, an isothiazolyl group, a thiazolyl group, a 1,2,4-thiadiazolyl group, a 1,3,4-thiadiazolyl group, and a 1,2,5-thiadiazolyl group, wherein each optionally is substituted with 1-2 $C_{1-6}$ alkyl groups.

By way of example, $(Ar)_m$, $(Ar)_{m'}$, and $(Ar)_{m''}$ can be selected from:

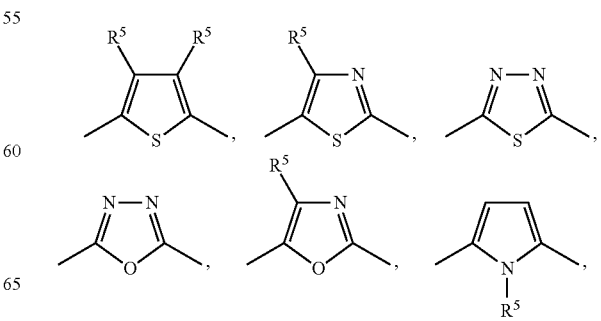

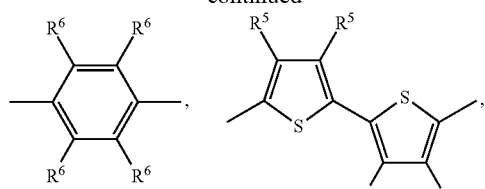

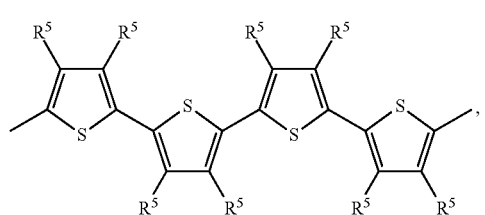

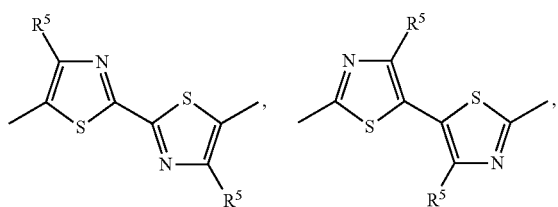

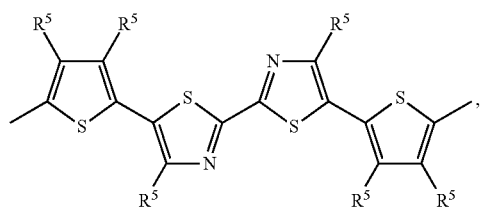

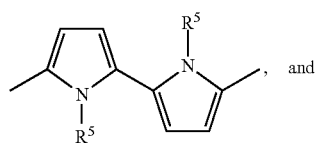

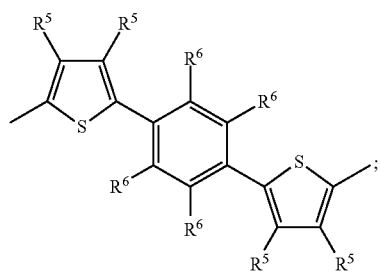

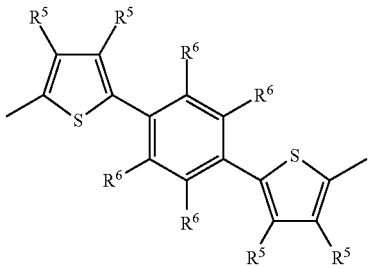

by itself or as part of

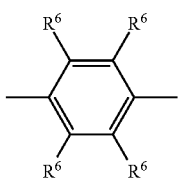

can be selected from:

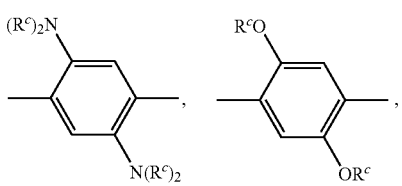

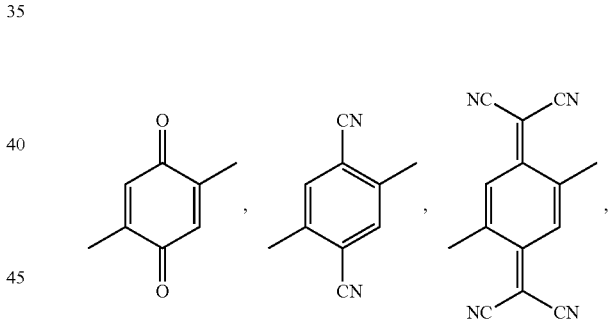

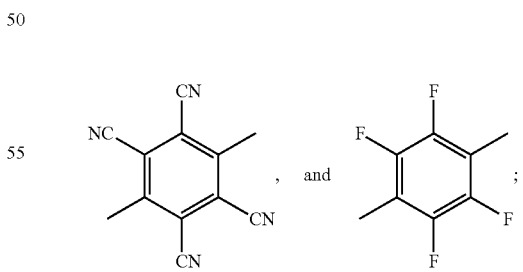

wherein $R^5$, at each occurrence, independently can be H or $R^a$; and $R^6$, at each occurrence, independently can be H or $R^a$, or alternatively, can be an oxo group or a $=C(R^a)_2$ group, where $R^a$ is as defined hereinabove. For example, $R^5$, at each occurrence, independently can be selected from H, a halogen, —CN, a $C_{1-40}$ alkyl group, and a $C_{1-40}$ haloalkyl group, and wherein $R^c$ is as defined herein. For example, $R^c$ can be selected from H, a $C_{1-6}$ alkyl group, and a —$C_{1-6}$ alkyl-$C_{6-14}$ aryl group.

Accordingly, in certain embodiments, the polymers of the present teachings can include repeating units having one or both of the formulae below:

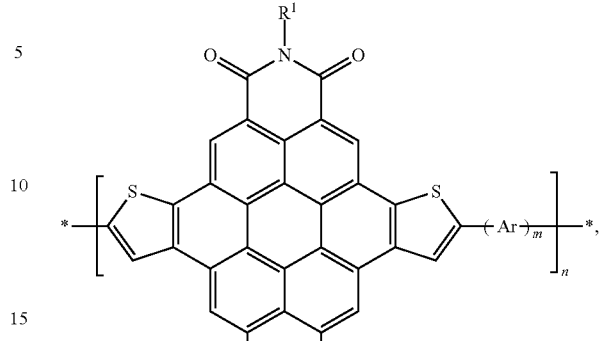

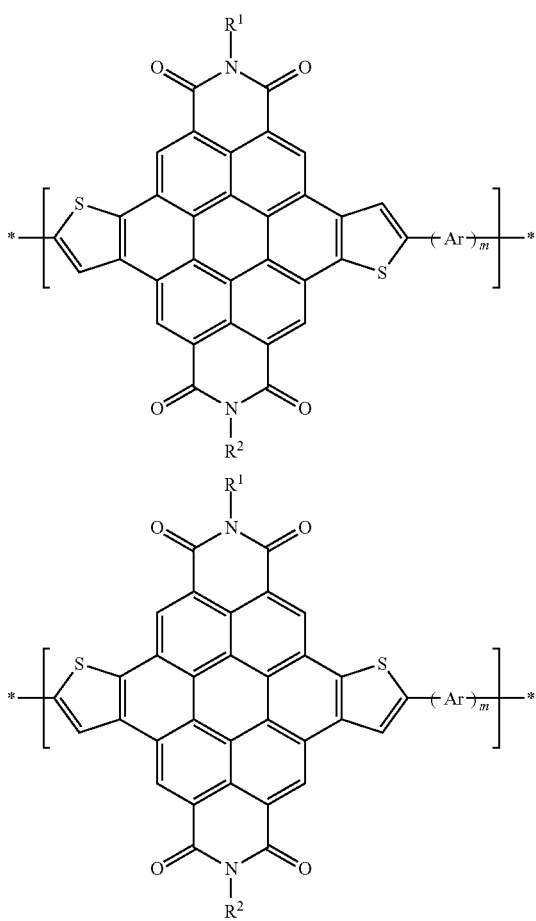

where Ar, at each occurrence, independently can be an optionally substituted 5- or 6-membered aryl or heteroaryl group; and $R^1$, $R^2$, and m are as defined herein.

For example, particular embodiments of the present copolymers can have formula III or IV:

III

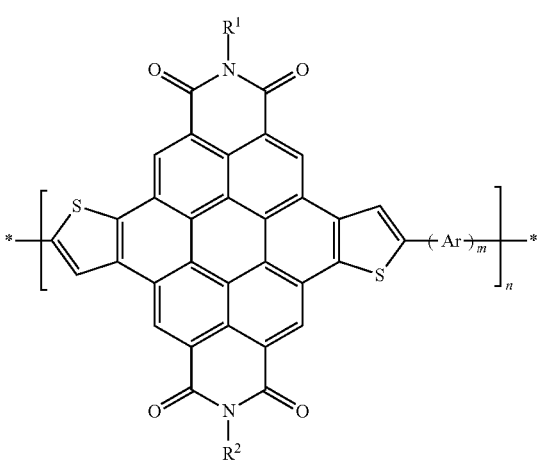

IV

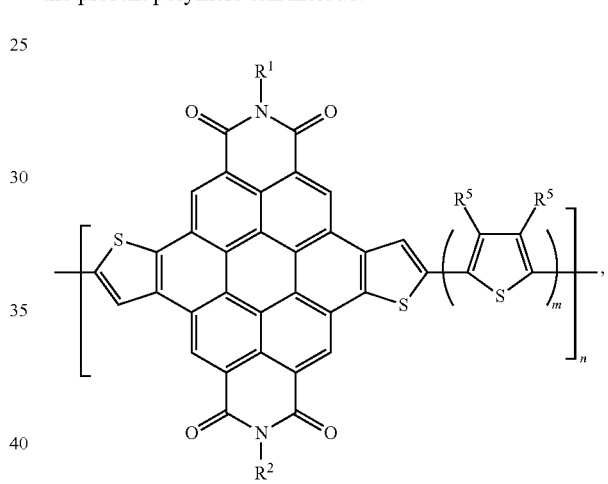

where Ar, $R^1$, $R^2$, m and n are as defined herein. Specifically, the present polymers can include:

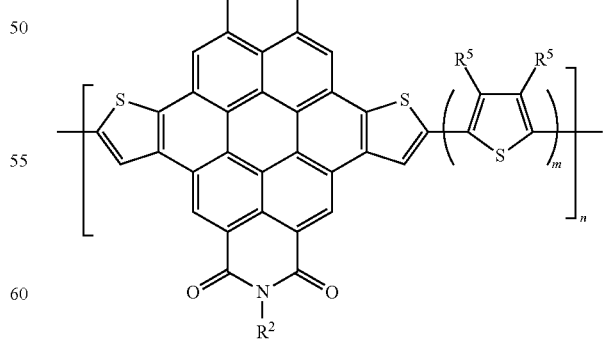

wherein $R^1$, $R^2$, $R^5$, m, and n are as defined herein. For example, $R^5$, at each occurrence, independently can be selected from H, a halogen, —CN, a $C_{1-40}$ alkyl group, and a $C_{1-40}$ haloalkyl group.

In particular embodiments, the present polymers can include:

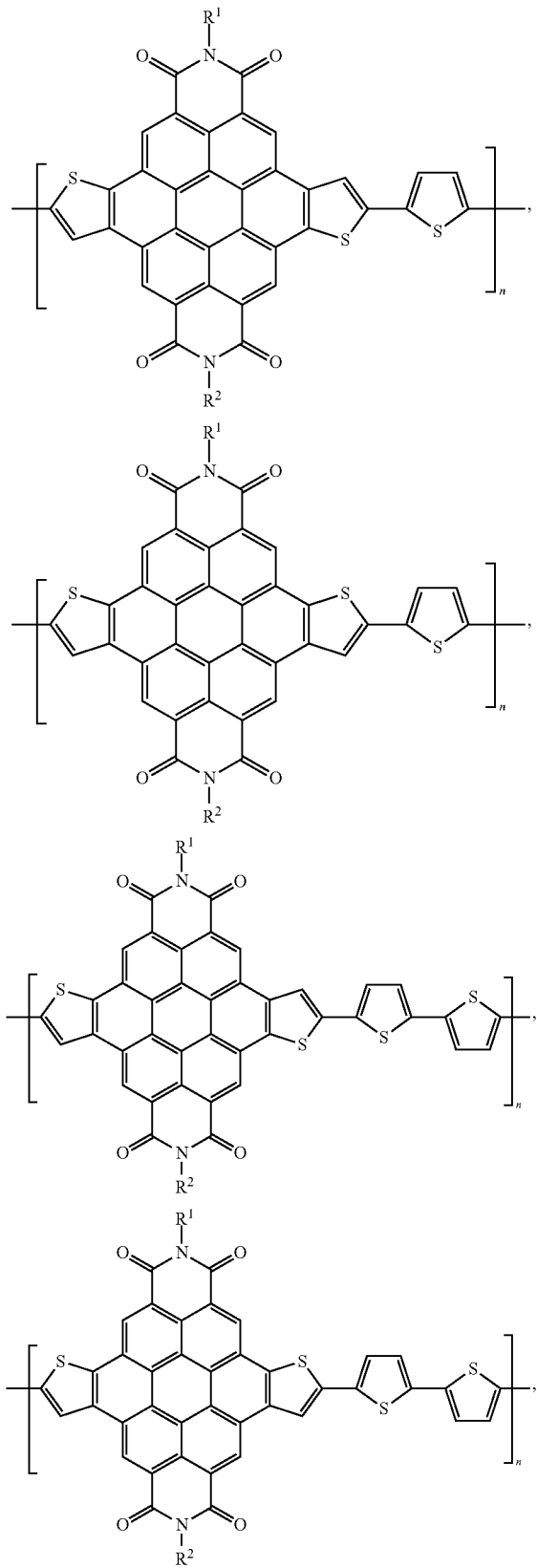

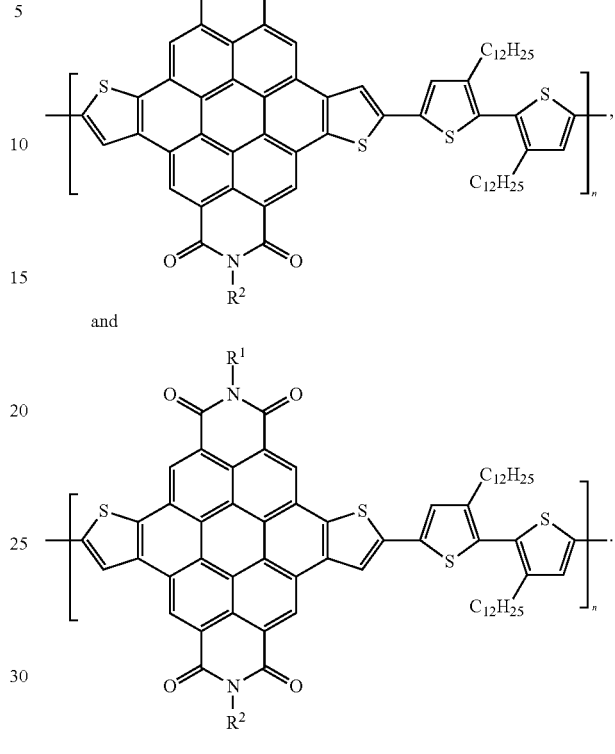

and where $R^1$ and $R^2$, independently can be a linear or branched $C_{1-40}$ alkyl or haloalkyl group, and n is greater than 2. For example, n can be an integer in the range of 2 to 5,000, 2 to 1,000, 2 to 500, 2 to 400, 2 to 300, or 2 to 200. In certain embodiments, n can be 2-100. In some embodiments, n can be an integer between 3 and 1,000. In certain embodiments, n can be 4-1,000, 5-1,000, 6-1,000, 7-1,000, 8-1,000, 9-1,000, or 10-1,000. For example, n can be 8-500, 8-400, 8-300, or 8-200. In certain embodiments, n can be 8-100.

More specifically, an embodiment of the present copolymers can have the formula:

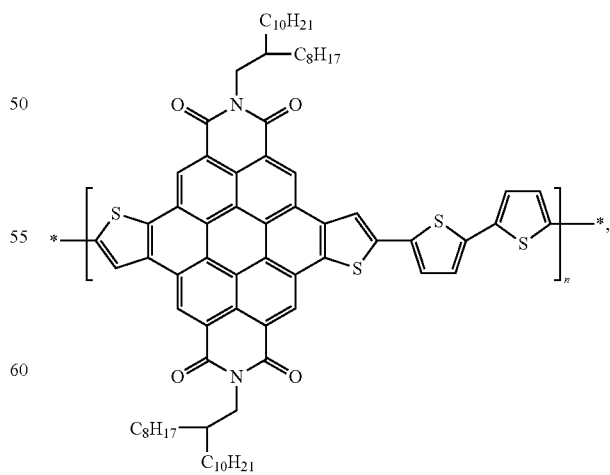

where n is an integer in the range of 2-1000, 3-1000, 4-1000, or 5-1000.

In various embodiments, the comonomer $M_2$ can include one or more optionally substituted fused ring moieties (π-2), optionally in combination with one or more Ar moieties and/or one or more conjugated linear linkers (Z) as described herein. In certain embodiments, the one or more optionally substituted fused ring moities can be covalently linked to other moieties in the copolymer via carbon atoms.

In some embodiments, π-2 can have a planar and highly conjugated cyclic core. Examples of suitable cyclic cores include naphthalene, anthracene, tetracene, pentacene, perylene, pyrene, coronene, fluorene, indacene, indenofluorene, and tetraphenylene, as well as their analogs in which one or more carbon atoms can be replaced with a heteroatom such as O, S, Si, Se, N, or P.

In certain embodiments, π-2 can have two or more five-, six-, and/or seven-membered rings. For example, π-2 can be an optionally substituted $C_{8-20}$ aryl group or an optionally substituted 8-20 membered heteroaryl group.

In various embodiments, π-2 can have a reduction potential greater than (i.e., more positive than) −2.6 V. In certain embodiments, π-2 can have a reduction potential greater than or equal to about −2.2 V. In particular embodiments, π-2 can have a reduction potential greater than or equal to about −1.2 V.

For example, such fused ring moities can be selected from:

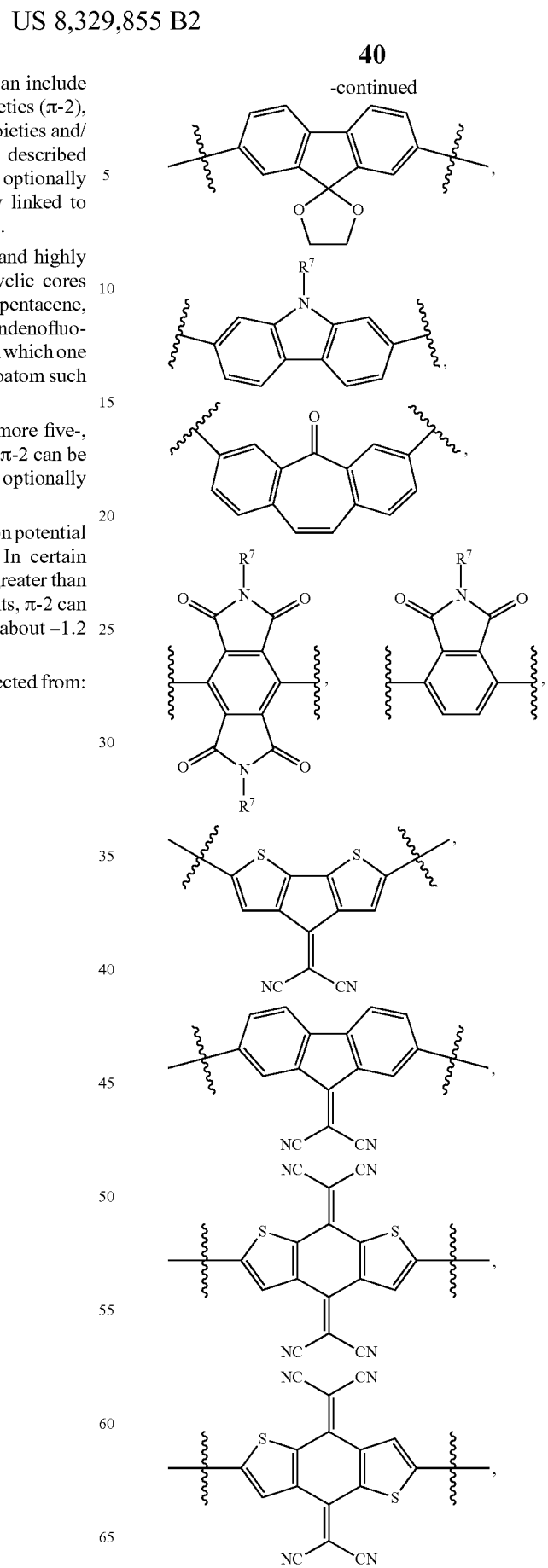

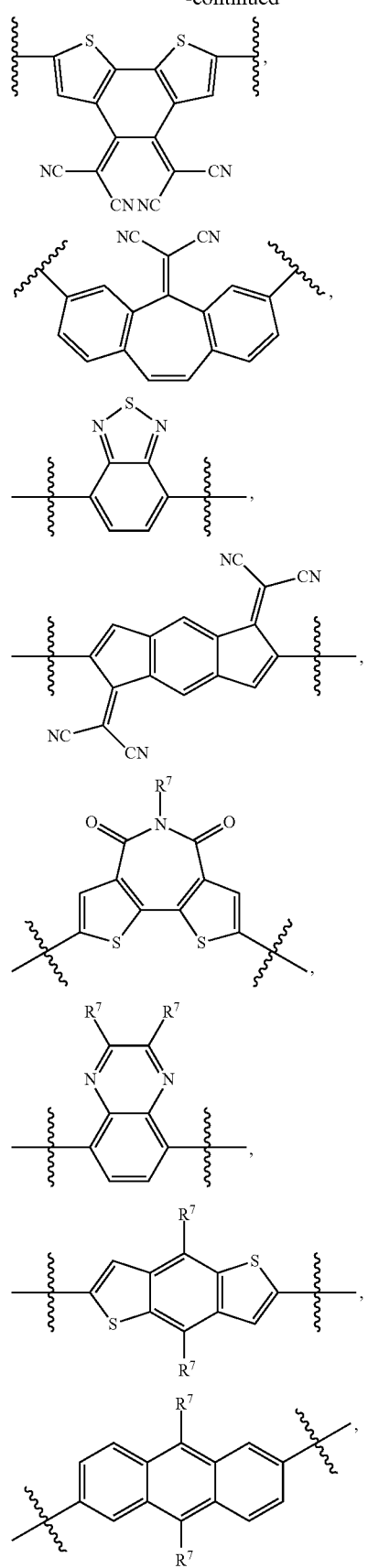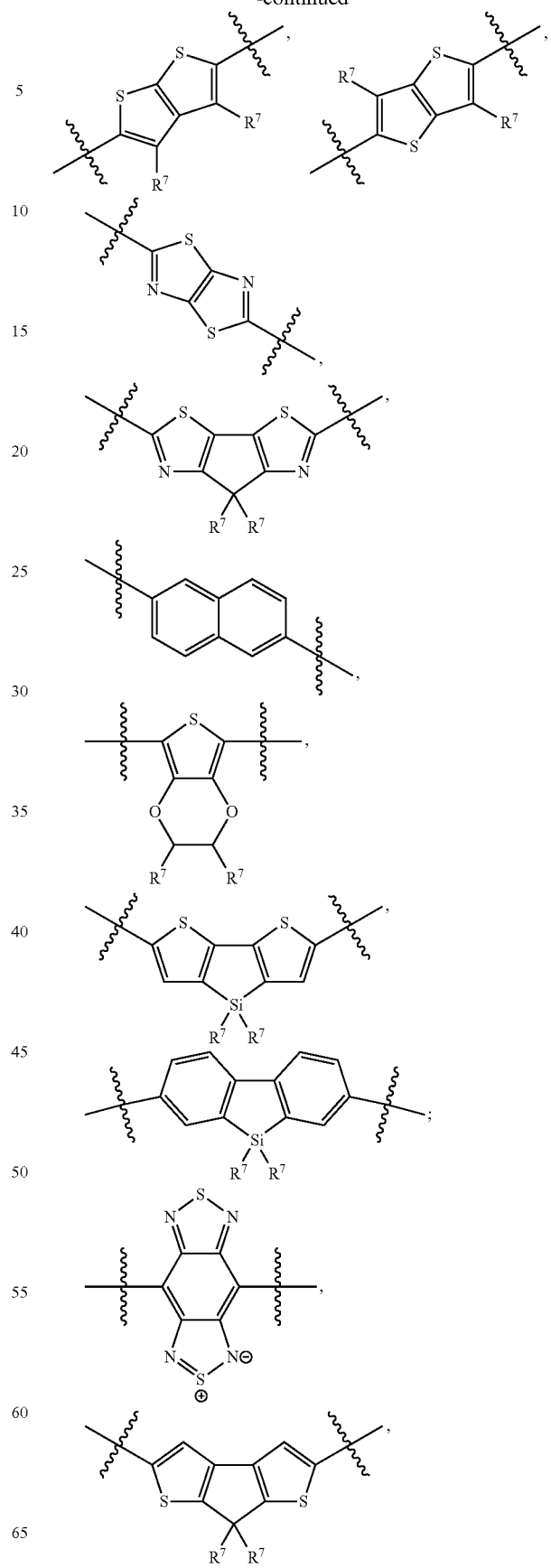

-continued

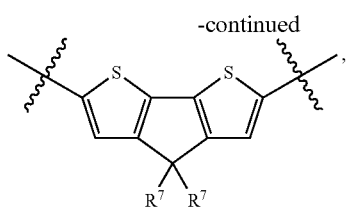

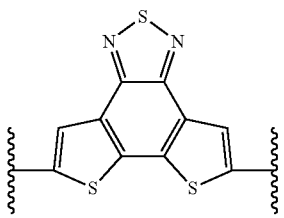

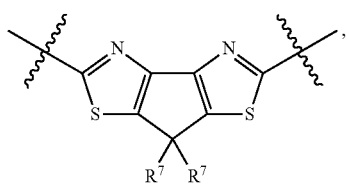

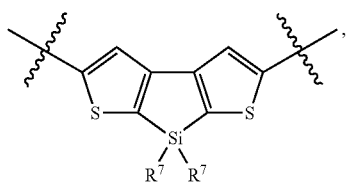

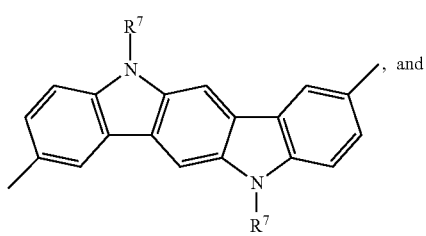, and

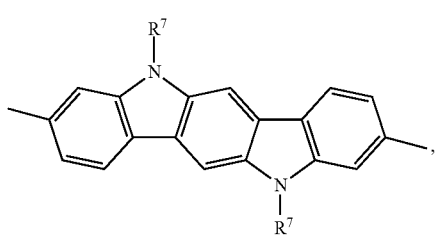

wherein $R^7$, at each occurrence, can be H or $R^a$. For example, $R^7$ can be selected from H, a $C_{1-40}$ alkyl group, and a $C_{1-40}$ haloalkyl group.

Particular embodiments of the polymers of the present teachings can have the formula:

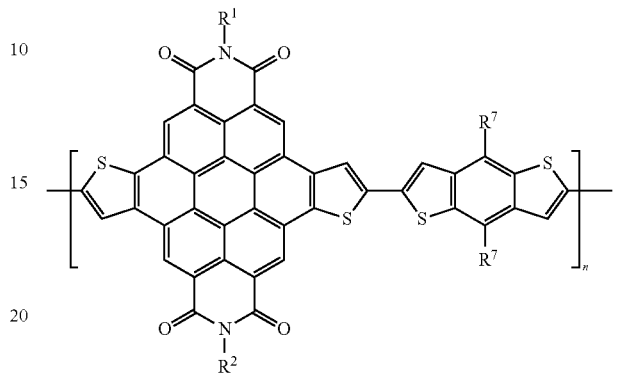

or

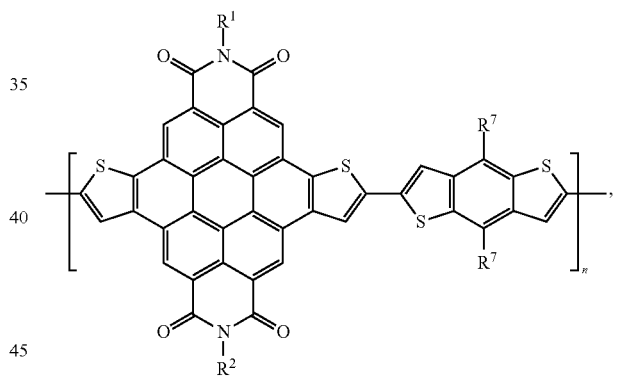

where $R^1$ and $R^2$, independently can be a linear or branched $C_{1-40}$ alkyl or haloalkyl group; $R^7$, at each occurrence, can be H or a linear or branched $C_{1-40}$ alkyl or haloalkyl group; and n is an integer in the range of 2 to 10,000. For example, n can be an integer in the range of 2 to 5,000, 2 to 1,000, 2 to 500, 2 to 400, 2 to 300, or 2 to 200. In certain embodiments, n can be 2-100. In some embodiments, n can be an integer between 3 and 1,000. In certain embodiments, n can be 4-1,000, 5-1,000, 6-1,000, 7-1,000, 8-1,000, 9-1,000, or 10-1,000. For example, n can be 8-500, 8-400, 8-300, or 8-200. In certain embodiments, n can be 8-100.

In certain embodiments, $M_2$ can be

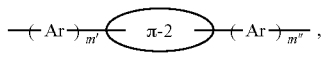

where Ar, π-2, m' and m" are as defined herein. Accordingly, the present polymers can have the formula V or VI:

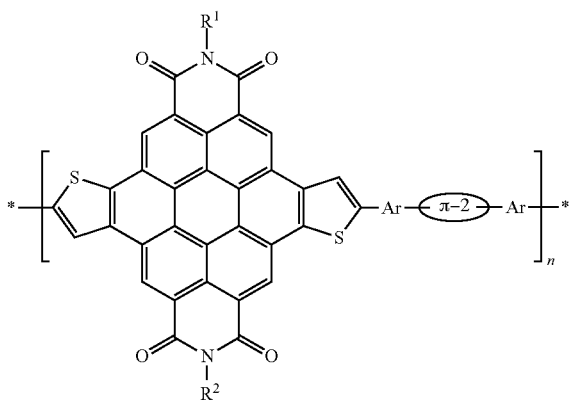

where R¹, R², Ar, π-2, and n are as defined herein. For example, R¹ and R², independently can be a linear or branched $C_{1-40}$ alkyl or haloalkyl group; Ar can be where $R^5$, at each occurrence, independently can be selected from H, a halogen, —CN, a $C_{1-40}$ alkyl group, and a $C_{1-40}$ haloalkyl group; n is an integer in the range of 2 to 10,000; and π-2 is as defined herein.

In various embodiments, the comonomer $M_2$ can include one or more linkers Z. The linker Z can be a conjugated system by itself (e.g., including two or more double or triple bonds) or can form a conjugated system with its neighboring components such as Ar, π-2, and/or a thienocoronene imide moiety. To illustrate, Z can be a divalent ethenyl group (i.e., having one double bond), a divalent ethynyl group (i.e., having one tripe bond), a $C_{4-40}$ alkenyl or alkynyl group that includes two or more conjugated double or triple bonds, or some other non-cyclic conjugated systems that can include heteroatoms such as Si, N, P, and the like. For example, Z can be selected from:

wherein $R^5$ is as defined herein. In certain embodiments, Z can be selected from:

For example, the present polymers can have the formula VII or VIII:

where $R^1$, $R^2$, Ar, Z, and n are as defined herein. For example, $R^1$ and $R^2$, independently can be a linear or branched $C_{1-40}$ alkyl or haloalkyl group; Ar can be

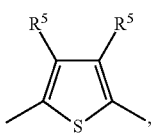

where R⁵, at each occurrence, independently can be selected from H, a halogen, —CN, a $C_{1-40}$ alkyl group, and a $C_{1-40}$ haloalkyl group; Z can be selected from:

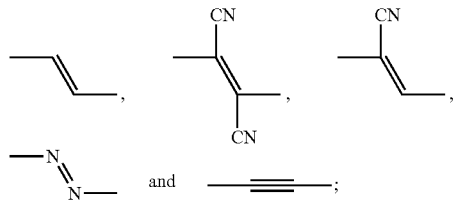

and n is an integer in the range of 2 to 10,000.

In certain embodiments, the comonomer $M_2$ can be

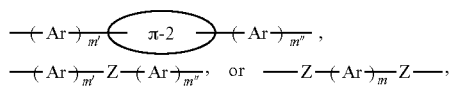

and can be selected from:

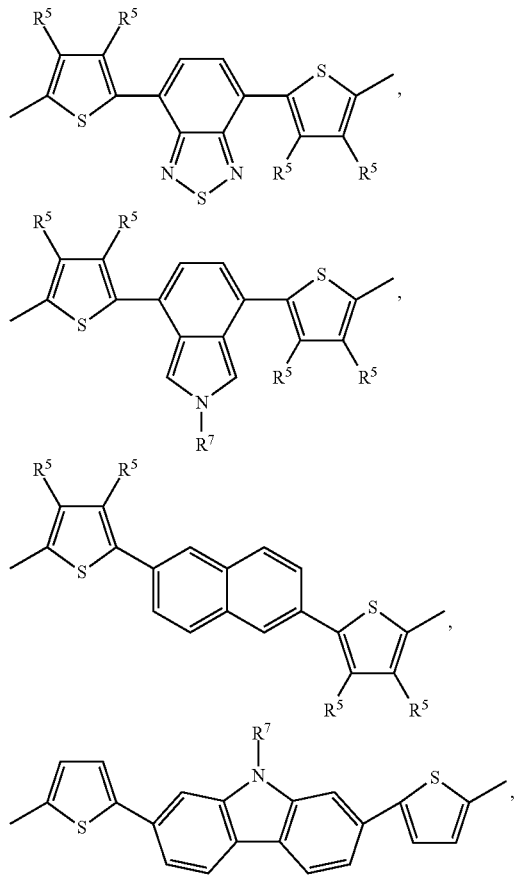

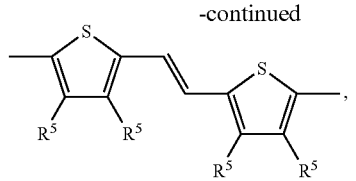

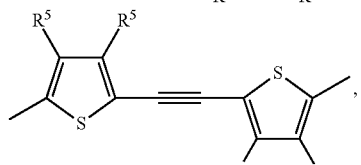

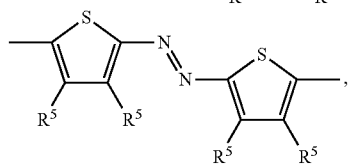

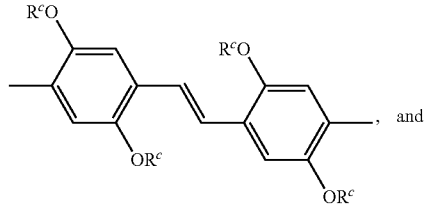

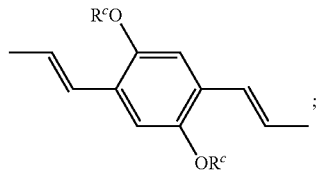

where R⁵, at each occurrence, independently can be selected from H, a halogen, —CN, a $C_{1-40}$ alkyl group, and a $C_{1-40}$ haloalkyl group; R⁷ can be selected from H, a halogen, —CN, a $C_{1-40}$ alkyl group, and a $C_{1-40}$ haloalkyl group; and $R^c$ can be selected from H, a $C_{1-6}$ alkyl group, and a —$C_{1-6}$ alkyl-$C_{6-14}$ aryl group.

In some embodiments, $M_2$ can be Z, that is, $M_2$ is

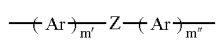

where both m' and m" are 0, and Z is as defined herein. For example, Z can be selected from:

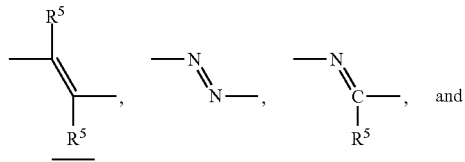

and, wherein R⁵ is as defined herein.

Compounds of the present teachings can be prepared according to procedures described in the procedure shown below. Alternatively, the present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the polymers described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Certain embodiments disclosed herein can be stable under ambient conditions ("ambient stable"), soluble in common solvents, and in turn solution-processable into various articles, structures, or devices. As used herein, a compound can be considered "ambient stable" or "stable at ambient conditions" when the carrier mobility or the reduction-potential of the compound is maintained at about its initial measurement when the compound is exposed to ambient conditions, for example, air, ambient temperature, and humidity, over a period of time. For example, a polymer according to the present teachings can be described as ambient stable if its carrier mobility or reduction potential does not vary more than 20% or more than 10% from its initial value after exposure to ambient conditions, including, air, humidity and temperature, over a 3 day, 5 day, or 10 day period. Without wishing to be bound by any particular theory, it is believed that the strong electron-depleted electronic structure of the thienocoronene moiety, and in the case of the polymers, the regioregular highly π-conjugated polymeric backbone, can make the present compounds ambient-stable n-channel semiconductor materials without requiring additional π-core functionalization (i.e., core substitution of the thienocoronene moiety) with strong electron-withdrawing functionalities.

As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl)ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone.

As used herein, "solution-processable" refers to compounds (e.g., thienocoronene-imide copolymers), materials, or compositions that can be used in various solution-phase processes including spin-coating, printing (e.g., inkjet printing, screen printing, pad printing, offset printing, gravure printing, flexographic printing, lithographic printing, massprinting and the like), spray coating, electrospray coating, drop casting, dip coating, and blade coating.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes a compound disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bactereriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices, such as thin film semiconductors, field effect transistors (e.g., thin film transistors), photovoltaics, photodetectors, organic light emitting devices such as organic light emitting diodes (OLEDs), complementary metal oxide semiconductors (CMOSs), complementary inverters, diodes, capacitors, sensors, D flip-flops, rectifiers, and ring oscillators, that make use of the compounds disclosed herein are within the scope of the present teachings as are methods of making the same. The present compounds can offer processing and operation advantages in the fabrication and/or the use of these devices. For example, articles of manufacture such as the various devices described herein can include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., described in Yoon, M-H. et al., *PNAS*, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which compounds of the present teachings are useful are photovoltaics or solar cells. Compounds of the present teachings can exhibit broad optical absorption and/or a very positively shifted reduction potential, making them desirable for such applications. Accordingly, the compounds described herein can be used as a n-type semiconductor in a photovoltaic design, which includes an adjacent p-type semiconductor material that forms a p-n junction. The compounds can be in the form of a thin film semiconductor, which can be deposited on a substrate to form a composite. Exploitation of polymers of the present teachings in such devices is within the knowledge of a skilled artisan.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

In certain embodiments, OTFT devices can be fabricated with the present compounds on doped silicon substrates, using $SiO_2$ as the dielectric, in top-contact geometries. In particular embodiments, the active semiconductor layer which incorporates at least a compound of the present teachings can be deposited at room temperature or at an elevated temperature. In other embodiments, the active semiconductor layer which incorporates at least one compound of the present teachings can be applied by spin-coating or printing as described herein. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present teachings can be deposited at room temperature or at an elevated temperature. In other embodiments, the active semiconducting layer which incorporates at least a compound of the present teachings can be applied by spin-coating or printing as described herein. Gate and source/drain contacts can be made of Au, other metals, or conducting polymers and deposited by vapor-deposition and/or printing.

The following examples are provided to illustrate further and to facilitate the understanding of the present teachings and are not in any way intended to limit the invention.

Example 1

Small Molecule Compound Synthesis

Example 1a

Synthesis of DTC8

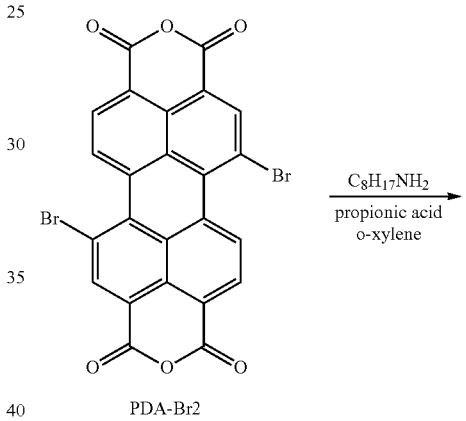

PDA-Br2

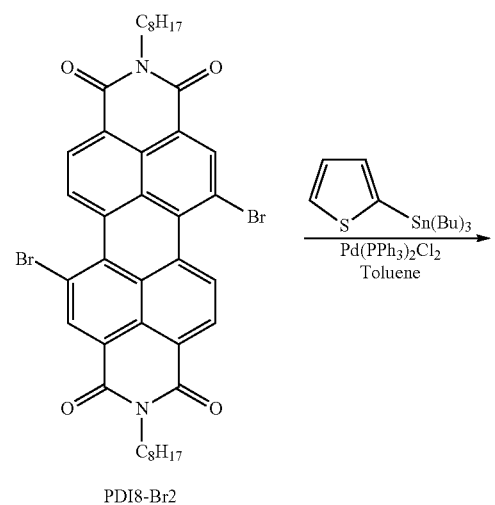

PDI8-Br2

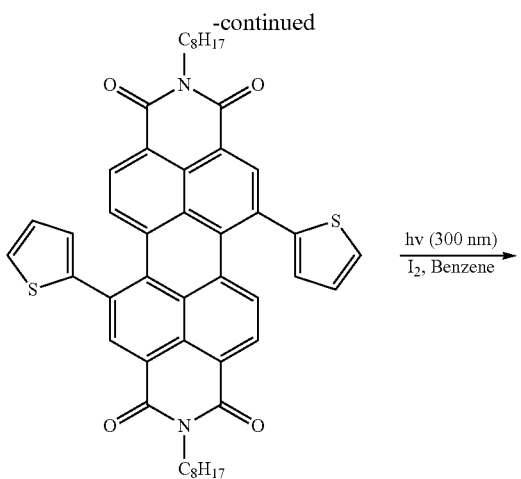

PDI8-T2

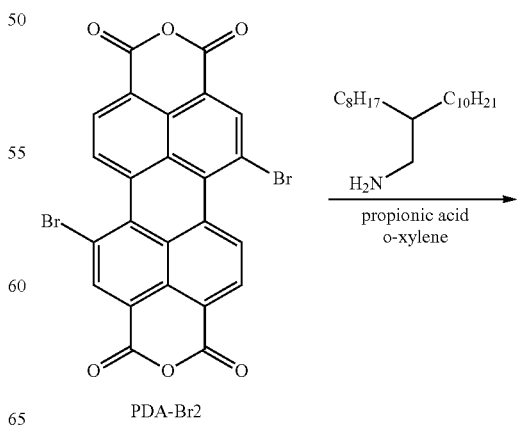

DTC8

Synthesis of PDI8-Br₂

A mixture of PDA-Br₂ (5.10 g, 9.27 mmol), octylamine (5.80 mL, 35.09 mmol), propionic acid (26 mL), and o-xylene (78 mL) was heated at 140° C. for 2 hours. The reaction mixture was then allowed to cool to room temperature, and methanol (~200 mL) was added. The precipitate was collected by vacuum filtration and dried in a vacuum oven (60° C., overnight). The crude mixture was purified by flash column chromatography (silica gel, chloroform) to afford PDI8-Br₂ as a deep red solid (5.73 g, 80% yield) (as a mixture of 1,6- and 1,7-dibromo isomers).

$^1$H NMR (CDCl₃ 500 MHz): δ: 9.49 (d, 2H, J=8.0 Hz), 8.93 (s, 2H), 8.73 (d, 2H, J=8.0 Hz), 4.22 (t, 4H), 1.72 (m, 4H), 1.23-1.44 (m, 20H), 0.88 (t, 6H).

Synthesis of PDI8-T2

The reagents PDI8-Br₂ (1.00 g, 1.29 mmol), 2-tributylstannylthiophene (1.41 mL, 4.41 mmol), and Pd(PPh₃)₂Cl₂ (200 mg, 0.27 mmol) were dissolved in dry toluene (100 mL) under nitrogen, and the reaction mixture was heated at 110° C. for 48 hours. After cooling to room temperature, the reaction mixture was evaporated to dryness to give a semi-solid crude product. The crude product was purified by column chromatography (silica gel, chloroform) to give the pure product as a deep purple solid (600 mg, 60% yield).

$^1$H NMR (CDCl₃ 500 MHz): δ: 8.60 (s, 2H), 8.23 (d, 2H, J=8.5 Hz), 7.98 (d, 2H, J=8.5 Hz), 7.50 (d, 2H, J=4.5 Hz), 7.32 (d, 2H, J=4.5 Hz), 7.20 (m, 2H), 4.20 (t, 4H), 1.73 (m, 4H), 1.25-1.45 (m, 20H), 0.87 (t, 6H). Anal. calcd. for (C₄₈H₄₆N₂O₄S₂): C, 74.00; N, 5.95; H, 3.60. Found: C, 73.92; N, 6.02; H, 3.61. m.p: 205-206° C.

Synthesis of DTC8

A mixture of PDI8-T2 (100 mg, 0.128 mmol) and iodine (68 mg, 0.256 mmol) was dissolved in benzene (80 mL), and vigorously bubbled with nitrogen for 30 minutes. The reaction mixture was exposed to the UV-light for 15 hours in a Rayonet RPR-100 photochemical reactor equipped with sixteen RPR 3000 Å lamps. After the photochemical reaction was done, the precipitate was filtered and washed successively with methanol, acetone and hexane, and dried in a vacuum oven (60° C., overnight) to afford the target compound as a deep red solid (55 mg, 55% yield). Anal. calcd. for (C₄₈H₄₂N₂O₄S₂): C, 74.39; N, 5.46; H, 3.61. Found: C, 74.38; N, 5.53; H, 3.61. MS (MALDI) m/z (M⁻): calcd for C₄₈H₄₂N₂O₄S₂, 774.99. found, 774.60. m.p: >400° C.

Example 1b

Synthesis of DTC2OD

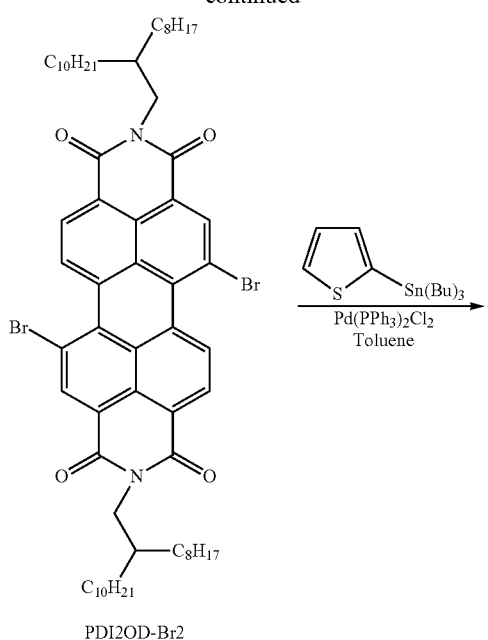

PDI2OD-Br2

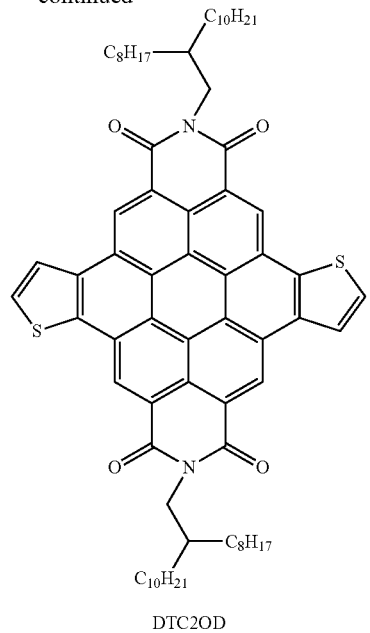

DTC2OD

Synthesis of PDI2OD-Br₂

A mixture of PDA-Br₂ (3.48 g, 6.33 mmol), 2-octyldodecylamine (5.65 g, 18.99 mmol), propionic acid (7.9 mL), and o-xylene (24.0 mL) was heated at 140° C. for 24 hours in a sealed flask. The reaction mixture was then allowed to cool to room temperature, and concentrated on a rotary evaporator. The crude mixture was purified by flash column chromatography (silica gel, chloroform) to afford PDI2OD-Br2 as a deep red solid (4.91 g, 70% yield) (as a mixture of 1,6- and 1,7-dibromo isomers).

$^1$H NMR (CDCl₃ 500 MHz): δ: 9.51 (d, 2H, J=8.0 Hz), 8.95 (s, 2H), 8.71 (d, 2H, J=8.0 Hz), 4.16 (d, 4H, J=7.0 Hz), 2.01 (m, 2H), 1.25-1.42 (m, 64H), 0.82-0.90 (m, 12H).

Synthesis of PDI2OD-T2

The reagents PDI2OD-Br2 (1.83 g, 1.65 mmol), 2-tributylstannylthiophene (2.10 mL, 6.60 mmol), and Pd(PPh₃)₂Cl₂ (347 mg, 0.49 mmol) were dissolved in dry toluene (100 mL) under nitrogen, and the reaction mixture was heated at 110° C. for 40 hours. After cooling to room temperature, the reaction mixture was evaporated to dryness to give a semi-solid crude product. The crude product was purified by column chromatography (silica gel, chloroform), to give the pure product as a deep purple solid (1.70 g, 92% yield).

$^1$H NMR (CDCl₃ 500 MHz): δ: 8.64 (s, 2H), 8.25 (d, 2H, J=8.5 Hz), 8.04 (d, 2H, J=8.5 Hz), 7.51 (d, 2H, J=4.5 Hz), 7.35 (d, 2H, J=4.5 Hz), 7.21 (m, 2H), 4.15 (d, 4H, J=7.0 Hz), 2.00 (m, 2H), 1.24-1.40 (m, 64H), 0.85-0.89 (m, 12H). Anal. calcd. for (C₇₂H₉₄N₂O₄S₂): C, 77.51; N, 8.49; H, 2.51. Found: C, 77.42; N, 8.29; H, 2.54.

Synthesis of DTC2OD

A mixture of PDI2OD-T2 (90 mg, 0.081 mmol) and iodine (41 mg, 0.161 mmol) was dissolved in benzene (90 mL), and exposed to the UV-light for 15 hours in a Rayonet RPR-100 photochemical reactor equipped with sixteen RPR 3000 Å lamps. After the photochemical reaction was done, the reac-

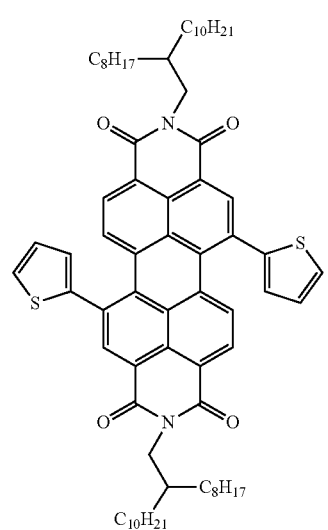

PDI2OD-T2 hv (300 nm), Benzene ↓ tion mixture was evaporated to dryness on a rotary evaporator and then purified by flash column chromatography (silica gel, chloroform) to afford the pure compound as a deep red solid (50 mg, 56% yield).

$^1$H NMR (CDCl$_3$ 500 MHz): δ: 8.48 (s, b, 2H), 8.29 (s, b, 2H), 7.88 (s, b, 2H), 7.80 (s, b, 2H), 4.18 (s, b, 4H), 2.07 (s, b, 2H), 1.26-1.40 (m, 64H), 0.85-0.88 (m, 12H). $^{13}$C NMR (CDCl$_3$): δ 14.19, 14.24, 22.76, 22.82, 26.63, 29.51, 29.58, 29.85, 29.89, 29.93, 30.02, 30.46, 31.85, 32.03, 32.10, 37.25, 44.85, 116.97 (b m), 117.70 (b m), 119.20 (b m), 119.39 (b m), 122.16 (b m), 122.77 (b m), 123.30 (b m), 128.79, 134.47, 134.49, 136.50, 136.55, 136.62, 162.52, 162.75 ppm. Anal. calcd. for (C$_{72}$H$_{90}$N$_2$O$_4$S$_2$): C, 77.79; N, 8.16; H, 2.52. Found: C, 77.89; N, 7.92; H, 2.57. m.p: 358-359° C.; MS (MALDI) m/z (M$^-$): calcd for C$_{72}$H$_{90}$N$_2$O$_4$S$_2$, 1110.63. found, 1111.03.

Example 1c

Synthesis of DTC2OD-Br2

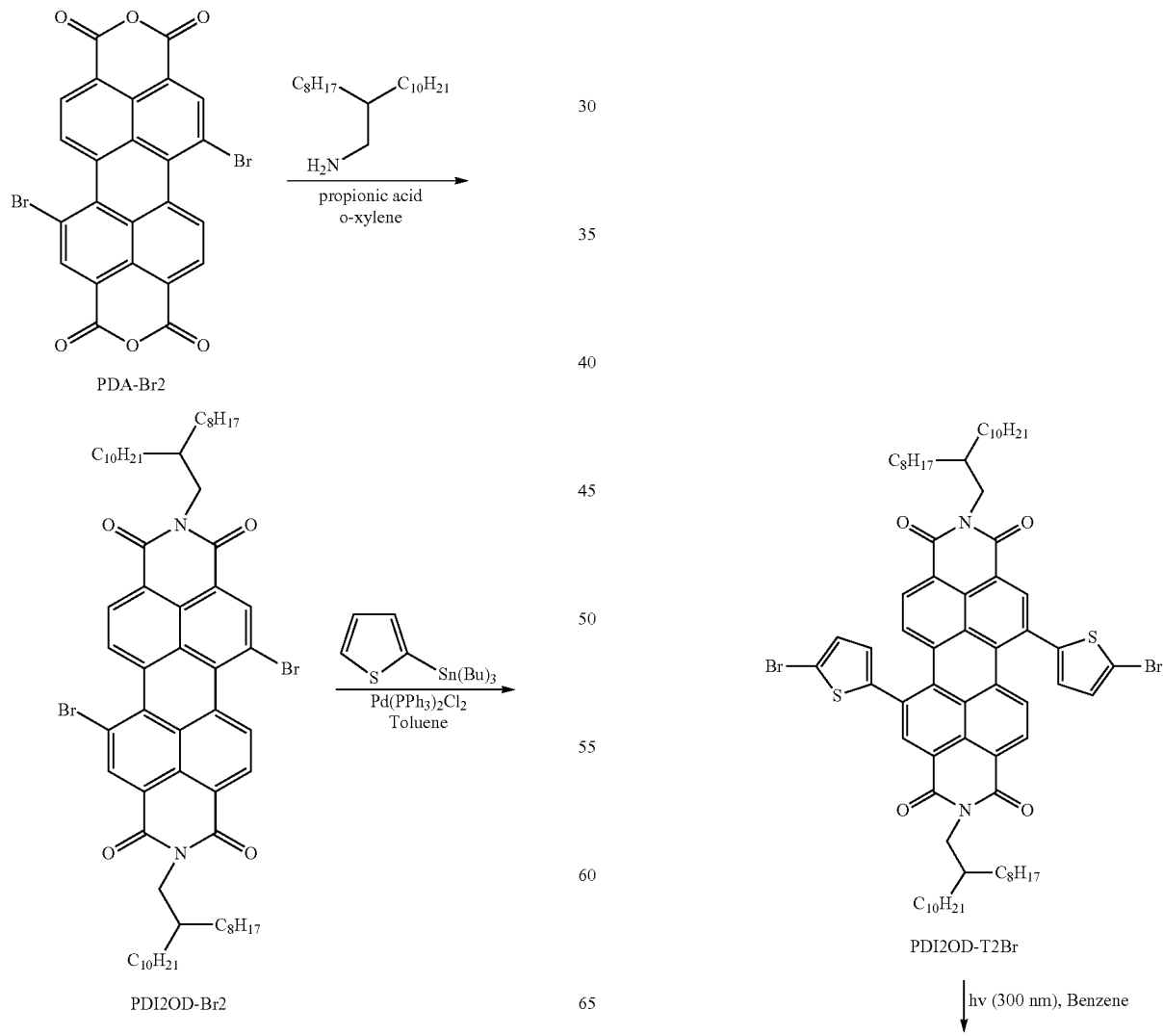

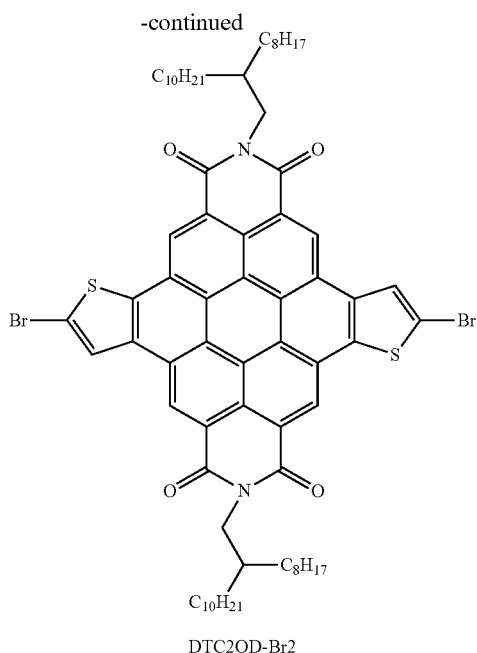

DTC2OD-Br2

Synthesis of PDI2OD-T2Br2

A mixture of PDI2OD-T2 (1.95 g, 1.75 mmol) and NBS (1.12 g, 6.29 mmol) in dry DMF (100 mL) was heated at 110° C. for 17 hours under nitrogen. After cooling to room temperature, the reaction mixture was evaporated to dryness to give a semi-solid crude product. The crude product was initially purified by column chromatography (silica gel, dichloromethane:hexanes (2:1, v/v)) to give a mixture of 1,6 and 1,7 isomers which were separated after a second column chromatography (silica gel, dichloromethane:hexanes (1:1, v/v)) to yield pure 1,7 isomer as a deep purple solid (1.0 g, 45% yield).

$^1$H NMR (CDCl$_3$ 500 MHz): δ: 8.54 (s, 2H), 8.32 (d, 2H, J=8.0 Hz), 8.13 (d, 2H, J=8.0 Hz), 7.18 (d, 2H, J=4.0 Hz), 7.15 (d, 2H, J=4.0 Hz), 4.14 (d, 4H, J=7.0 Hz), 2.00 (m, 2H), 1.24-1.44 (m, 64H), 0.84-0.89 (m, 12H). $^{13}$C NMR (CDCl$_3$): δ 14.20, 22.74, 26.54, 29.38, 29.42, 29.66, 29.71, 30.11, 31.70, 31.95, 31.98, 36.69, 44.84, 115.14, 122.30, 122.42, 125.34, 127.84, 128.04, 128.27, 128.90, 129.08, 129.78, 129.92, 131.70, 132.08, 132.87, 133.97, 135.38, 137.92, 145.08, 163.32, 163.48 ppm. Anal. calcd. for (C$_{72}$H$_{92}$Br$_2$N$_2$O$_4$S$_2$): C, 67.91; N, 7.28; H, 2.20. Found: C, 67.99; N, 7.17; H, 2.15.

Synthesis of DTC2OD-Br2

A mixture of PDI2OD-T2Br2 (347 mg, 0.272 mmol) and iodine (147 mg, 0.552 mmol) was dissolved in benzene (200 mL), and exposed to the UV-light for 15 hours in a Rayonet RPR-100 photochemical reactor equipped with sixteen RPR 3000 Å lamps. After the photochemical reaction was done, the precipitate was filtered and washed successively with methanol, acetone and hexane, and dried in a vacuum oven (60° C., overnight) to afford the pure compound as an orange solid (326 mg, 94% yield).

$^1$H NMR (CDCl$_3$ 500 MHz): δ: 9.00 (s, b, 2H), 8.77 (s, b, 2H), 8.11 (s, b, 2H), 4.35 (s, b, 4H), 2.10 (s, b, 2H), 1.19-1.55 (m, 64H), 0.81-0.83 (m, 12H). Anal. calcd. for (C$_{72}$H$_{88}$Br$_2$N$_2$O$_4$S$_2$): C, 68.12; N, 6.99; H, 2.21. Found: C, 68.27; N, 7.14; H, 2.33. m.p: >400° C.; MS (MALDI) m/z (M): calcd for C$_{72}$H$_{88}$Br$_2$N$_2$O$_4$S$_2$, 1269.42. found, 1268.48.

Example 2

Thienocoronene-Based Polymer Synthesis

Example 2a

Synthesis of P(DTC2OD)

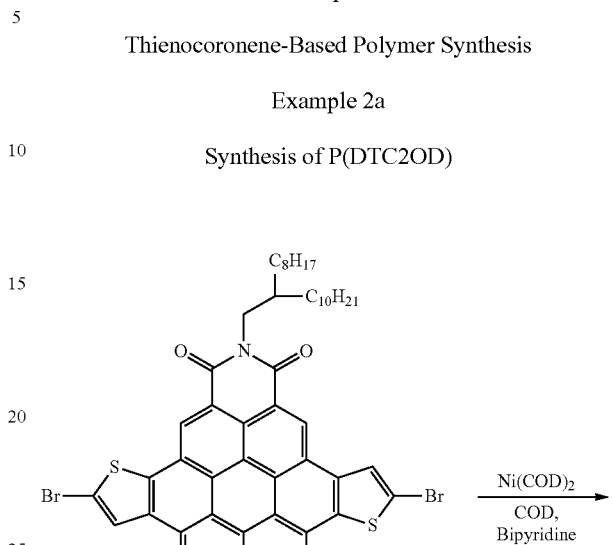

DTC2OD-Br2

P(DTC2OD)

1,5-Cyclooctadiene (COD, 9.3 mg, 0.086 mmol), Ni(COD)$_2$ (23.7 mg, 0.086 mmol), and 2,2'-bipyridyl (13.4 mg, 0.086 mmol) were mixed in dry DMF (2 mL) and dry toluene (3 mL). The purple solution was heated at 80° C. for 30 minutes. DTC2OD-Br2 (50 mg, 0.039 mmol) in 6 mL of dry toluene was added. The solution was stirred under nitrogen for 17 hours. The reaction mixture was poured into methanol (4 N HCl) and filtered.

Example 2b
Synthesis of P(DTC2OD-T2)
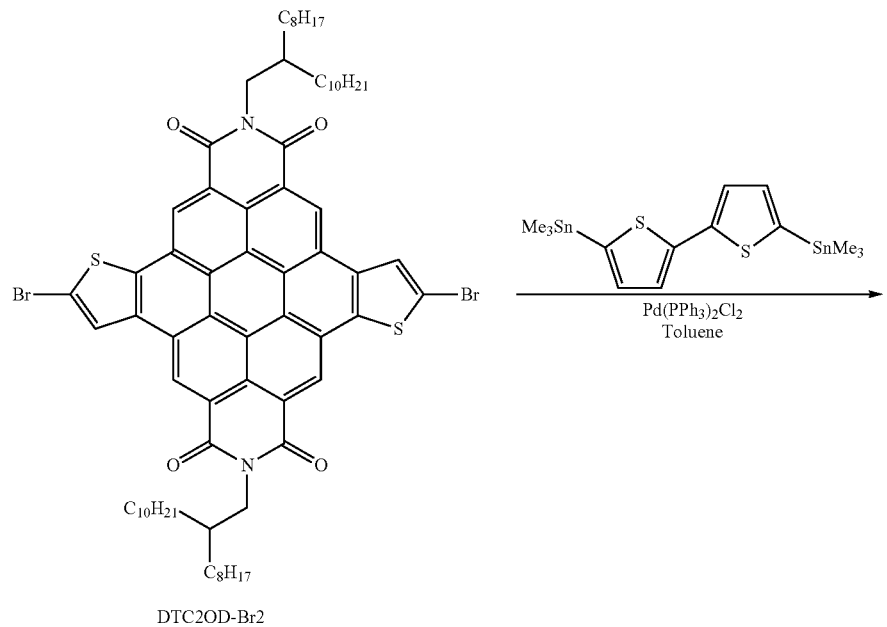
DTC2OD-Br2
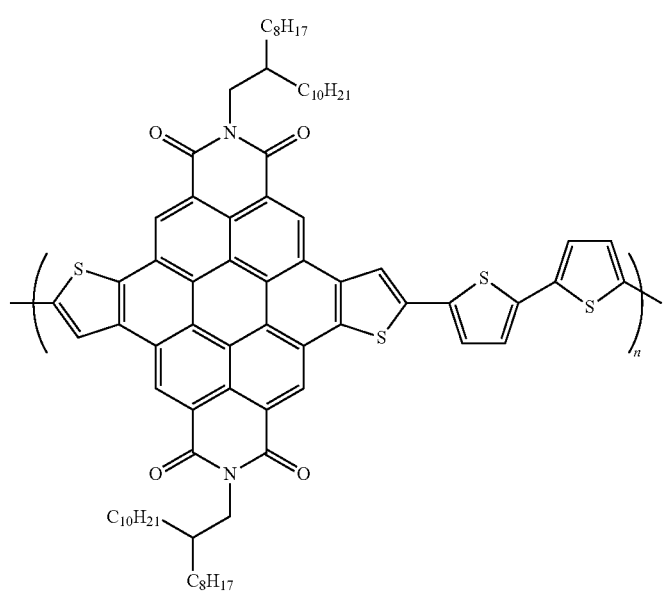
P(DTC2OD-T2)

Synthesis of P(DTC2OD-T2)

The reagents 5,5'-bis(trimethylstannyl)-2,2'-bithiophene (11.6 mg, 0.024 mmol), DTC2OD-Br2 (30 mg, 0.024 mmol), and Pd(PPh$_3$)$_2$Cl$_2$ (0.8 mg, 0.0012 mmol) in anhydrous toluene (4 mL) were heated at 90° C. for 19 h under nitrogen in a sealed flask. After cooling to room temperature, the dark green viscous reaction mixture was poured into methanol (20 mL). After stirring for 2 hours, the precipitated dark solid was collected by gravity filtration.

Example 3

Characterization of Small Molecules and Polymers

Table 1 below provides optical absorption data of certain embodiments of the present compounds in chloroform solution, as well as the optical band gaps estimated from the low energy band edge.

TABLE 1

| Compound | $\lambda_{abs}$ (nm) | $E_g$ (eV) |
|---|---|---|
| PDI2OD | 525 | 2.30 |
| DTC2OD | 469 | 2.32 |

To investigate the redox properties of the present compounds, cyclic voltammetry experiments were performed using a THF—(NBu)$_4$PF$_6$ solvent-electrolyte solution, Pt as the working electrode, silver as the pseudo reference electrode and ferrocene (0.54 V vs SCE) as the internal standard. The Pt working electrode was coated with a thin polymer film by drop-casting a CHCl$_3$ solution. Exemplary redox potential data including estimated frontier molecular orbital energies are provided in Table 2.

TABLE 2

| Compound | $E_{red-1}^{onset}$ (V) | $E_{ox-1}^{onset}$ (V) | $E_{HOMO}^{b}/E_{LUMO}^{c}$ (eV) |
|---|---|---|---|
| PDI2OD | −0.52$^a$ | — | −6.22/−3.92 |
| DTC2OD | −0.76$^a$ | — | −6.00/−3.68 |

$^a$Half-wave first reduction potential.
$^b$E$_{HOMO}$ calculated as: −(E$_{ox-1}^{onset}$ + 4.44 eV) or calculated from: E$_g$ = LUMO − HOMO if oxidation peak is not observed.
$^c$E$_{LUMO}$ calculated as: −(E$_{red-1}^{onset}$ + 4.44 eV).

Example 4

Device Fabrication and Characterization

The semiconducting properties of compounds of the present teachings were evaluated in top-gate bottom-contact transistor architectures.

A Keithley 4200 semiconductor characterization system was used to perform all electrical/TFT characterizations concerning the devices. The 4200 SCS system consists of three source measurement units (SMU), all of which are supplied with remote pre-amplifiers. The other major component of the test system is a Signatone probe station. Triax cable and probes were used for all electrodes to provide the first level of shielding. A dark/metal box enclosure was used to avoid light exposure and to further reduce environmental noise. The dark box had a triax cable feedthrough panel to maintain consistent triax shielding all the way from the preamps to the end of triax probe tips.

Transistor carrier mobilities (μ) were calculated by standard field effect transistor equations. In traditional metal-insulator-semiconductor FETs (MISFETs), there is typically a linear and saturated regime in the $I_{DS}$ vs $V_{DS}$ curves at different $V_G$ (where $I_{DS}$ is the source-drain saturation current, $V_{DS}$ is the potential between the source and drain, and $V_G$ is the gate voltage). At large $V_{DS}$, the current saturates and is given by:

$$(I_{DS})_{sat} = (WC_i/2L)\mu(V_G-V_t)^2 \quad (1)$$

where L and W are the device channel length and width, respectively, $C_i$ is the capacitance of the gate insulator, and $V_t$ is the threshold voltage. Mobilities (μ) were calculated in the saturation regime by rearranging equation (1):

$$\mu_{sat} = (2I_{DS}L)/[WC_i(V_G-V_t)^2] \quad (2)$$

The threshold voltage ($V_t$) can be estimated as the x intercept of the linear section of the plot of $V_G$ versus $(I_{DS})^{1/2}$.

Table 3 summarizes the transistor performance parameters measured under ambient conditions including the field-effect electron and hole mobilities (μ, in saturation unless indicated), current on-to-off ratio ($I_{on}$:$I_{off}$), and turn-on voltage ($V_{on}$) calculated from Vg=0 V to Vg=+/−60-80 V.

TABLE 3

| Compound | $\mu_{sat}(e^-)$ (cm$^2$/V·s) | $\mu_{sat}(h^+)$ (cm$^2$/V·s) | $I_{on}/I_{off}(e^-)$ | $I_{on}/I_{off}(h^+)$ | $V_{on}$(V) |
|---|---|---|---|---|---|
| DTC2OD | 1 × 10$^{-5}$ | 1 × 10$^{-5}$ | 1 × 10$^3$ | 1 × 10$^3$ | +60, −80 |

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A polymer comprising identical or different repeating units having the formula:

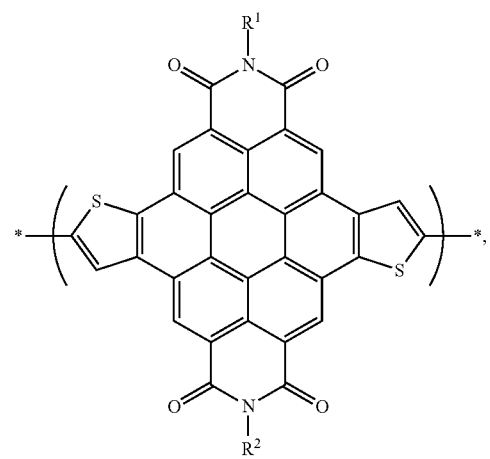

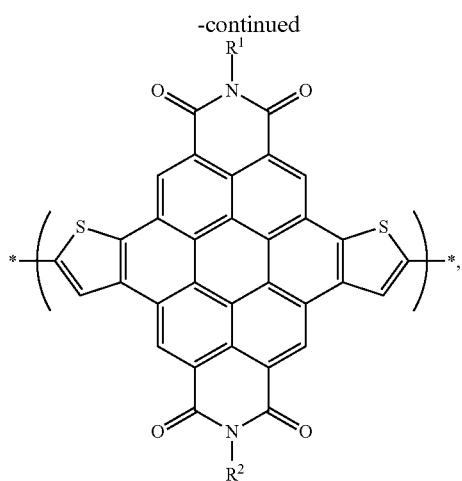

or both,
wherein:
R¹ and R² independently are selected from H, a $C_{1-40}$ alkyl group, a $C_{2-40}$ alkenyl group, a $C_{1-40}$ haloalkyl group, -L'-Cy¹, -L'-Cy¹-L'-Cy², -L'-Cy¹-L'-Cy²—Cy², -L'-Cy¹—Cy¹, -L'-Cy¹—Cy¹-L'-Cy², -L'-Cy¹—Cy¹-L'-Cy²—Cy², -L'-Cy¹-L-R, -L'-Cy¹-L'-Cy²-L-R, -L'-Cy¹-L'-Cy²—Cy²-L-R, -L'-Cy¹—Cy¹-L-R, and -L'-Cy¹—Cy¹-L'-Cy²-L-R, wherein:
each of the $C_{1-40}$ alkyl group, the $C_{2-40}$ alkenyl group, and the $C_{1-40}$ haloalkyl group optionally is substituted with 1-10 substituents independently selected from a halogen, —CN, NO₂, OH, —NH₂, —NH($C_{1-40}$ alkyl), —N($C_{1-40}$ alkyl)₂, —S(O)₂OH, —CHO, —C(O)—$C_{1-40}$ alkyl, —C(O)OH, —C(O)—O$C_{1-40}$ alkyl, —C(O)NH₂, —C(O)NH—$C_{1-40}$ alkyl, —C(O)N($C_{1-40}$ alkyl)₂, —O$C_{1-40}$ alkyl, —SiH₃, —SiH($C_{1-40}$ alkyl)₂, —SiH₂($C_{1-40}$ alkyl), and —Si($C_{1-40}$ alkyl)₃;

each of the $C_{1-40}$ alkyl group, the $C_{2-40}$ alkenyl group, and the $C_{1-40}$ haloalkyl group can be bonded covalently to the imide nitrogen atom via an optional linker;

R is selected from a $C_{1-40}$ alkyl group, a $C_{2-40}$ alkenyl group, and a $C_{1-40}$ haloalkyl group, each of which optionally is substituted with 1-10 substituents independently selected from a halogen, —CN, NO₂, OH, —NH₂, —NH($C_{1-40}$ alkyl), —N($C_{1-40}$ alkyl)₂, —S(O)₂OH, —CHO, —C(O)—$C_{1-40}$ alkyl, —C(O)OH, —C(O)—O$C_{1-40}$ alkyl, —C(O)NH₂, —C(O)NH—$C_{1-40}$ alkyl, —C(O)N($C_{1-40}$ alkyl)₂, —O$C_{1-40}$ alkyl, —SiH₃, —SiH($C_{1-40}$ alkyl)₂, —SiH₂($C_{1-40}$ alkyl), and —Si($C_{1-40}$ alkyl)₃;

Cy¹ and Cy² independently are selected from a $C_{6-14}$ aryl group, a 5-14 membered heteroaryl group, a $C_{3-14}$ cycloalkyl group, and a 3-14 membered cycloheteroalkyl group, each of which optionally is substituted with 1-5 substituents independently selected from a halogen, —CN, oxo, =C(CN)₂, a $C_{1-6}$ alkyl group, a $C_{1-6}$ alkoxy group, and a $C_{1-6}$ haloalkyl group;

L is a covalent bond or a linker selected from —Y—O—Y—, —Y—[S(O)$_w$]—Y—, —Y—C(O)—Y—, —Y—[NR$^c$C(O)]—Y—, —Y—[C(O)NR$^c$]—Y—, —Y—NR$^c$—Y—, and —Y—[SiR$^c_2$]—Y—;

L', at each occurrence, independently is a covalent bond or a linker selected from —Y—O—Y—, —Y—[S(O)$_w$]—Y—, —Y—C(O)—Y—, —Y—[NR$^c$C(O)]—Y—, —Y—[C(O)NR$^c$]—, —Y—NR$^c$—Y—, —Y—[SiR$^c_2$]—Y—, a divalent $C_{1-40}$ alkyl group, a divalent $C_{2-40}$ alkenyl group, and a divalent $C_{1-40}$ haloalkyl group, wherein:
Y, at each occurrence, independently is selected from a divalent $C_{1-40}$ alkyl group, divalent $C_{2-40}$ alkenyl group, a divalent $C_{1-40}$ haloalkyl group, and a covalent bond;

R$^c$ is selected from H, a $C_{1-6}$ alkyl group, a $C_{6-14}$ aryl group, and a —$C_{1-6}$ alkyl-$C_{6-14}$ aryl group; and w is 0, 1, or 2;

wherein the polymer has a degree of polymerization (n) that is greater than 2.

2. The polymer of claim 1, wherein the polymer is a homopolymer consisting of repeating units having the formula:

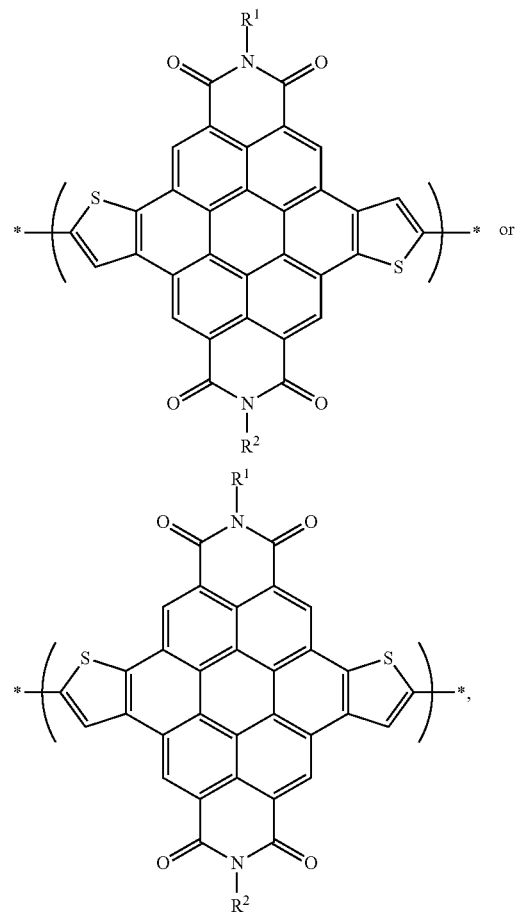

wherein R¹ and R² are as defined in claim 1.

3. A copolymer represented by the formula:

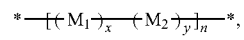

wherein:

$M_1$ has the formula:

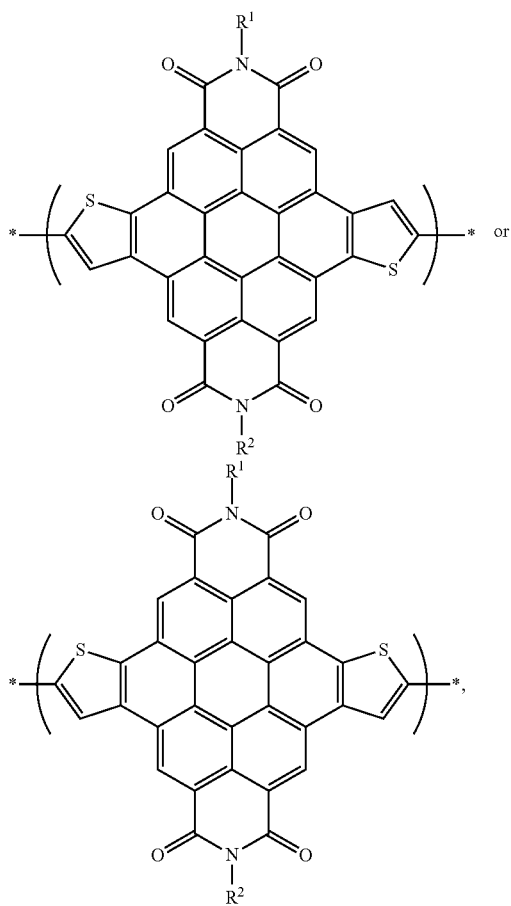

or $M_2$ has a formula selected from:

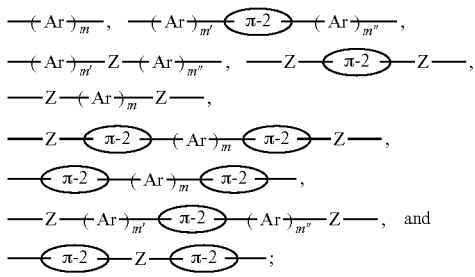

wherein:

$R^1$ and $R^2$ independently are selected from a $C_{1-40}$ alkyl group, a $C_{2-40}$ alkenyl group, and a $C_{1-40}$ haloalkyl group, wherein:

each of the $C_{1-40}$ alkyl group, the $C_{2-40}$ alkenyl group, and the $C_{1-40}$ haloalkyl group optionally is substituted with 1-10 substituents independently selected from a halogen, —CN, —NO$_2$, —OH, —NH$_2$, —NH(C$_{1-40}$ alkyl), —N(C$_{1-40}$ alkyl)$_2$, —S(O)$_2$OH, —CHO, —C(O)—C$_{1-40}$ alkyl, —C(O)OH, —C(O)—OC$_{1-40}$ alkyl, —C(O)NH$_2$, —C(O)NH—C$_{1-40}$ alkyl, —C(O) N(C$_{1-40}$ alkyl)$_2$, —OC$_{1-40}$ alkyl, —SiH$_3$, —SiH (C$_{1-40}$ alkyl)$_2$, —SiH$_2$(C$_{1-40}$ alkyl), and —Si(C$_{1-40}$ alkyl)$_3$; and each of the $C_{1-40}$ alkyl group, the $C_{2-40}$ alkenyl group, and the $C_{1-40}$ haloalkyl group can be bonded covalently to the imide nitrogen atom via an optional linker;

π-2, at each occurrence, independently is an optionally substituted fused ring moiety;

Ar, at each occurrence, independently is an optionally substituted monocyclic moiety;

Z, at each occurrence, independently is a conjugated linear linker;

m, at each occurrence, is 1, 2, 3, 4, 5 or 6;

m' and m", at each occurrence, independently are 0, 1, 2, 3, 4, 5 or 6;

n is an integer in the range of 2 to 10,000; and x and y represent the molar fraction of $M_1$ and the molar fraction of $M_2$, respectively.

4. The polymer of claim 3 having formula III, IV, V, VI, VII, or VIII:

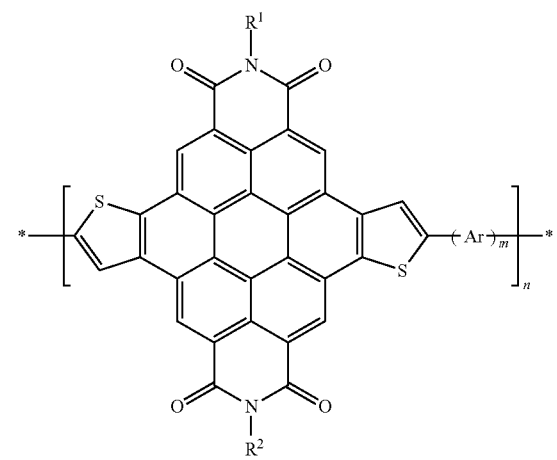

III

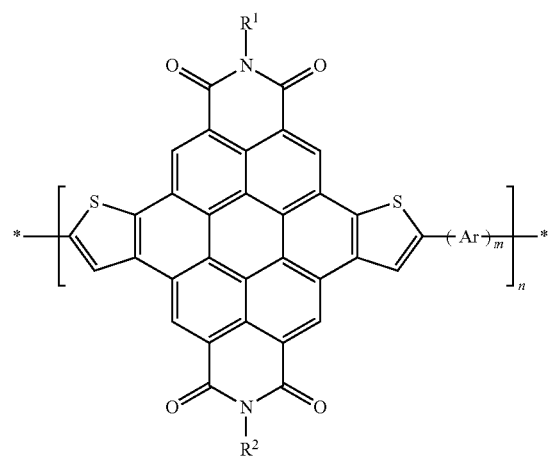

IV wherein R¹, R², Ar, π-2, Z, m and n are as defined in claim 3.

5. The polymer according to claim 3, wherein $M_2$ is $$-(Ar)_m-$$

and is selected from:

-continued
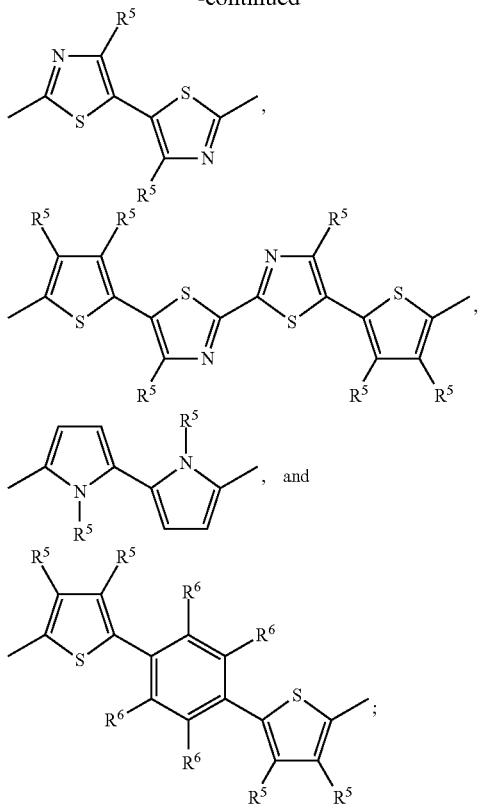
wherein R⁵ and R⁶, at each occurrence, independently are selected from H, a halogen, —CN, a C$_{1-40}$ alkyl group, and a C$_{1-30}$ haloalkyl group.
6. The polymer according to claim 3, wherein M$_2$ is
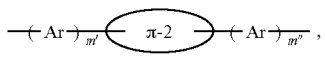
wherein π-2 is selected from:
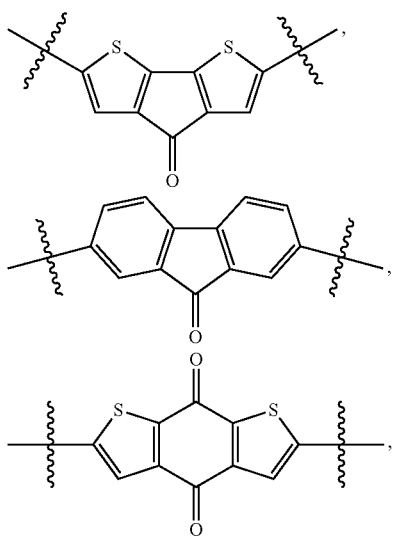
-continued
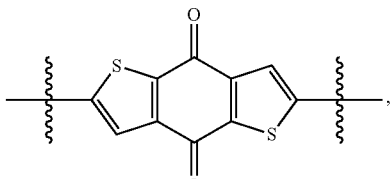
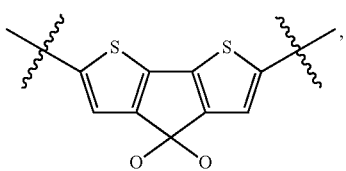
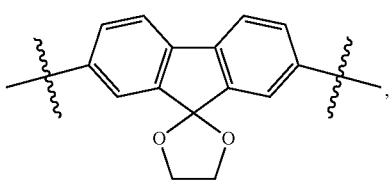
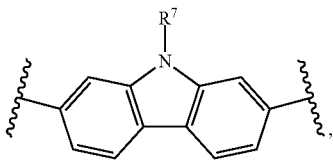
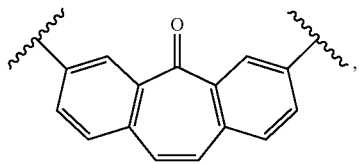
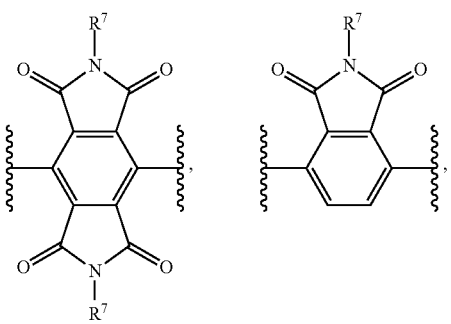
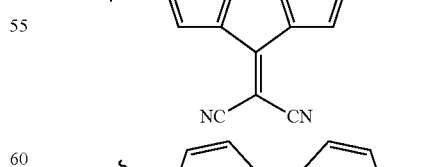
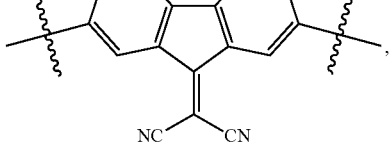

-continued
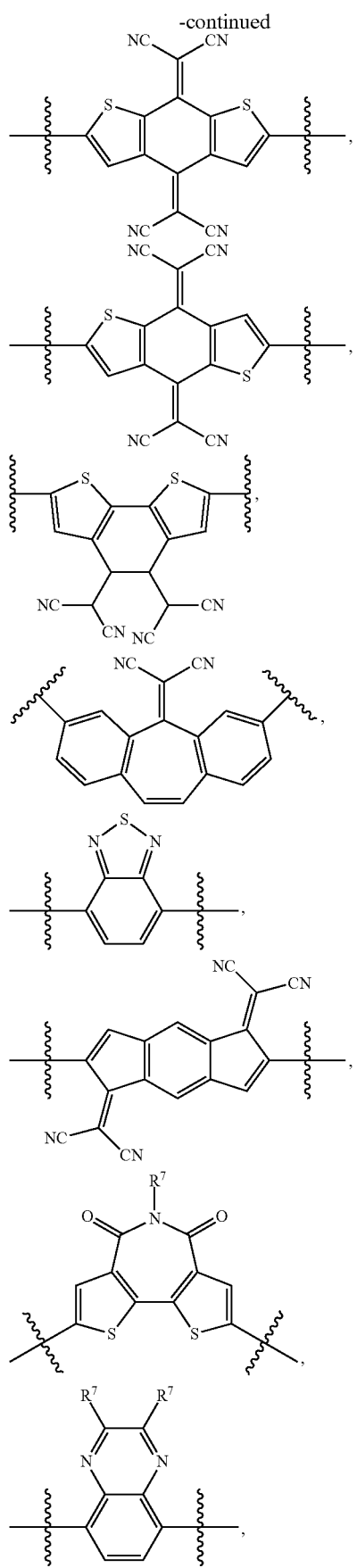
-continued
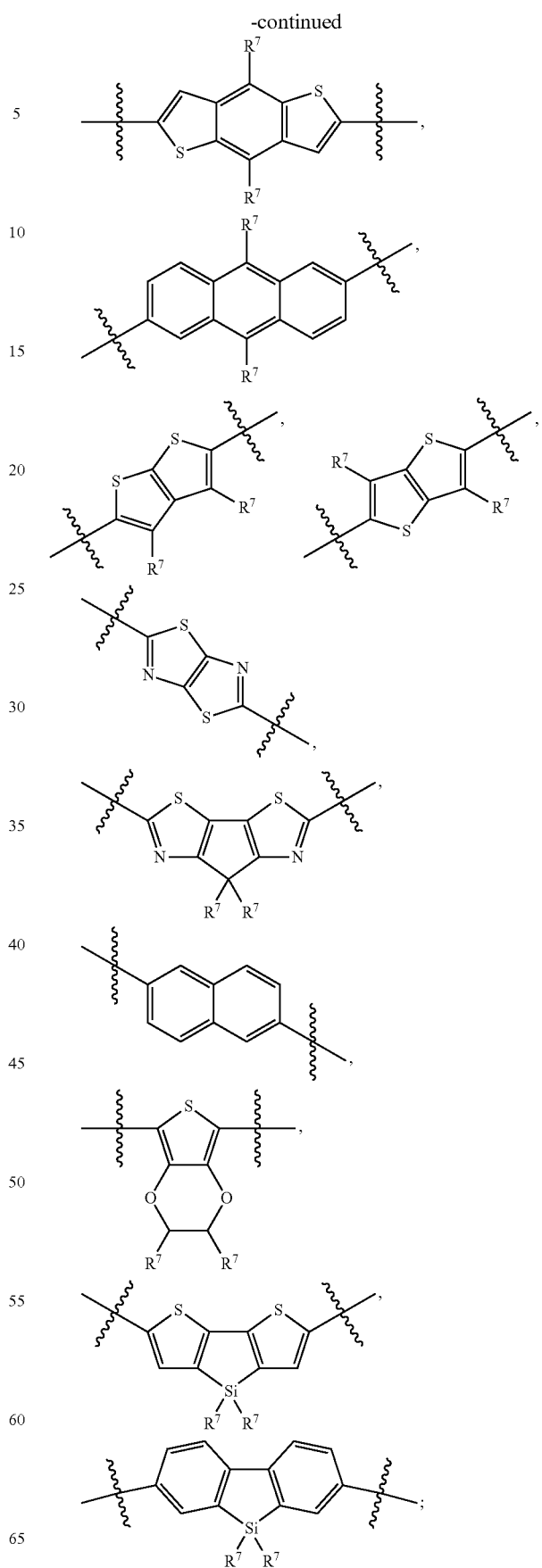

-continued
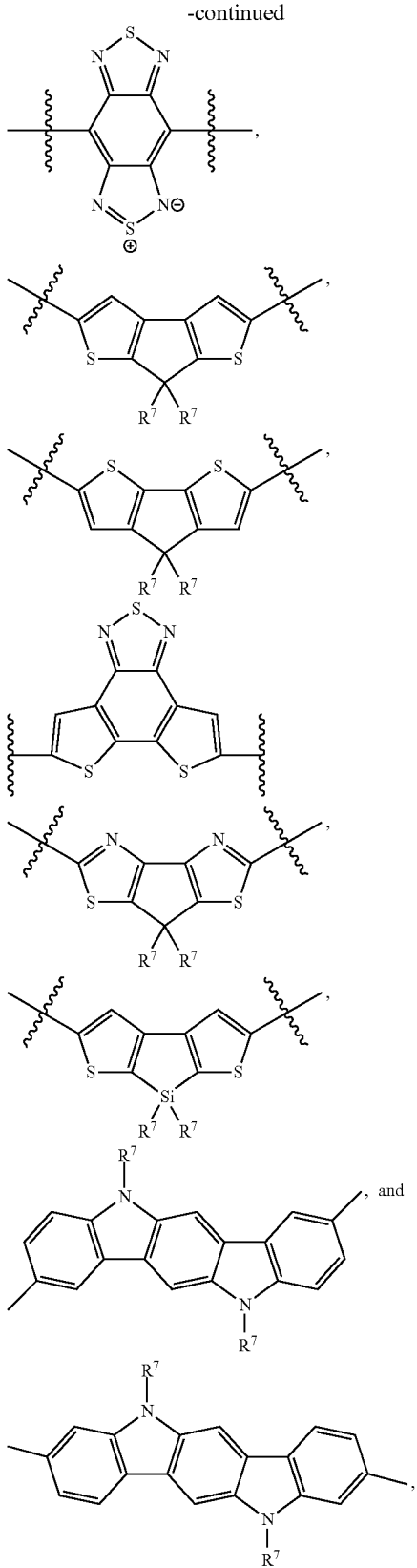
wherein R⁷ is selected from H, a halogen, —CN, a C$_{1-40}$ alkyl group, and a C$_{1-40}$ haloalkyl group, and Ar, m', and m" are as defined in claim 3.
7. The polymer according to claim 6, wherein m' and m" are 0.
8. The polymer according to claim 3, wherein M$_2$ is
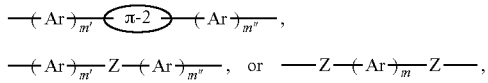
and is selected from:
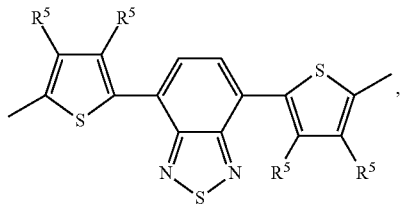
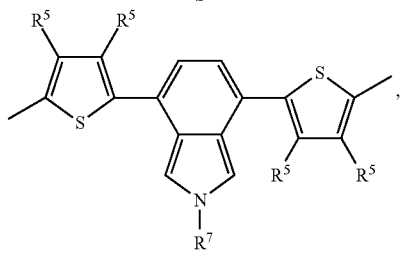
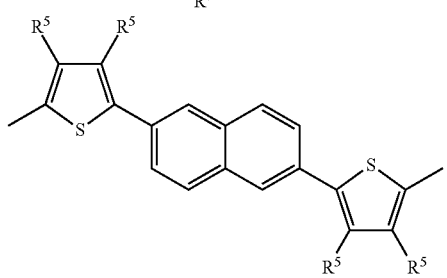
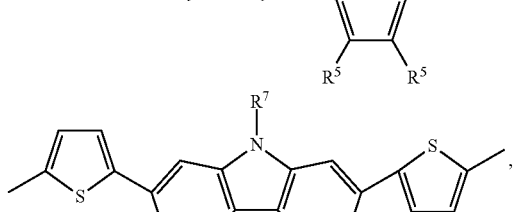
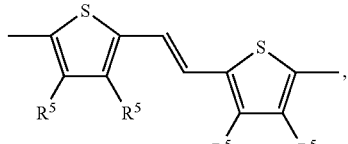
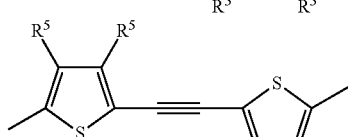
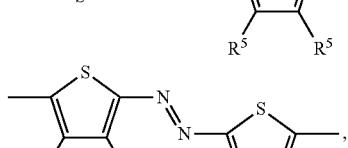
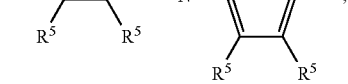

-continued

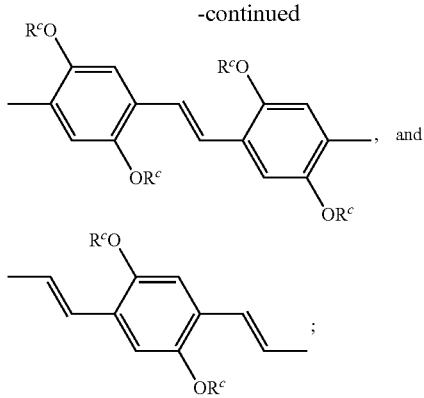

wherein $R^5$, at each occurrence, independently is selected from H, a halogen, —CN, a $C_{1-40}$ alkyl group, and a $C_{1-40}$ haloalkyl group; $R^7$ is selected from H, a $C_{1-40}$ alkyl group, and a $C_{1-40}$ haloalkyl group; and $R^c$ is selected from H, a $C_{1-6}$ alkyl group, and a —$C_{1-6}$ alkyl-$C_{6-14}$ aryl group.

9. A polymer selected from:

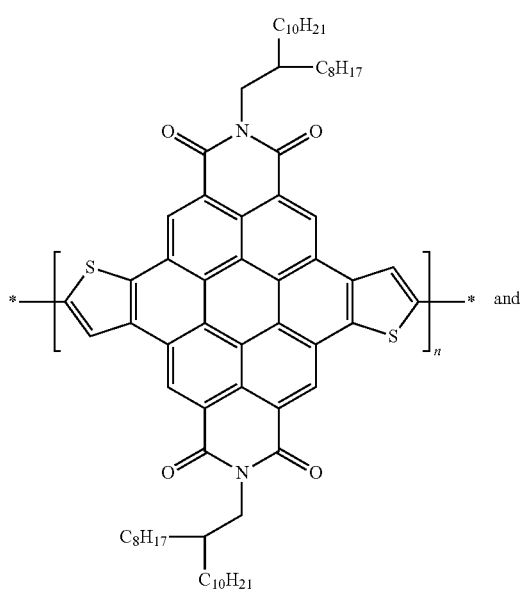

and

-continued

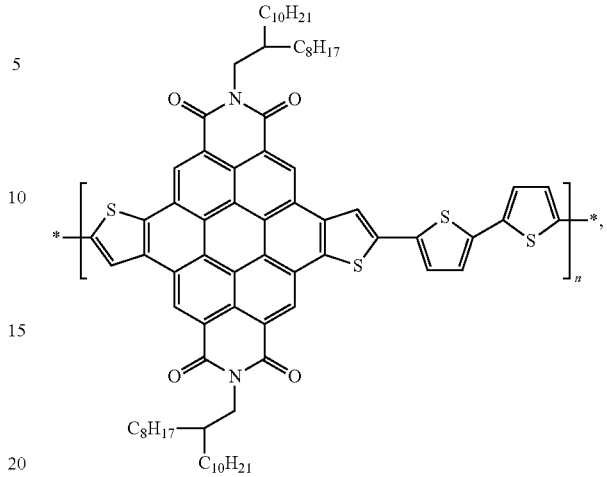

wherein n is an integer in the range of 2 to 10,000.

10. A thin film semiconductor comprising one or more polymers of claim 1.

11. An electronic, optical, or optoelectronic device comprising the thin film semiconductor of claim 10.

12. The polymer of claim 1, wherein $R^1$ and $R^2$ independently are a linear or branched $C_{1-40}$ alkyl or haloalkyl group.

13. The polymer of claim 3, wherein $R^1$ and $R^2$ independently are a linear or branched $C_{1-40}$ alkyl or haloalkyl group.

14. A thin film semiconductor comprising one or more polymers of claim 3.

15. An electronic, optical, or optoelectronic device comprising the thin film semiconductor of claim 14.

16. A thin film semiconductor comprising one or more polymers of claim 9.

17. An electronic, optical, or optoelectronic device comprising the thin film semiconductor of claim 16.

* * * * *